United States Patent
Cornelius et al.

(10) Patent No.: US 8,877,345 B2
(45) Date of Patent: Nov. 4, 2014

(54) NANOWIRES AND METHOD FOR THE PRODUCTION THERE OF

(75) Inventors: Thomas Cornelius, Grenoble (FR); Wolfgang Ensinger, Munster (DE); Reinhard Neumann, Dossenheim (DE); Markus Rauber, Darmstadt (DE)

(73) Assignee: GSI Helmholtzzentrum für Schwerionenforschung GmbH, Darmstadt (DE)

( * ) Notice: Subject to any disclaimer, the term of this patent is extended or adjusted under 35 U.S.C. 154(b) by 589 days.

(21) Appl. No.: 12/933,448
(22) PCT Filed: Mar. 12, 2009
(86) PCT No.: PCT/EP2009/001781
§ 371 (c)(1), (2), (4) Date: Apr. 5, 2011
(87) PCT Pub. No.: WO2009/115230
PCT Pub. Date: Sep. 24, 2009

(65) Prior Publication Data
US 2011/0174069 A1 Jul. 21, 2011

(30) Foreign Application Priority Data
Mar. 20, 2008 (DE) .......................... 10 2008 015 333

(51) Int. Cl.
G01F 1/688 (2006.01)
C25D 1/04 (2006.01)
(Continued)

(52) U.S. Cl.
CPC .. *C25D 1/00* (2013.01); *C25D 1/04* (2013.01); *C25D 5/18* (2013.01); *B01J 2219/0086* (2013.01); *B81B 2201/051* (2013.01); *B01J 2219/00783* (2013.01); *C25D 1/08* (2013.01); *C25D 1/003* (2013.01); *B01J 2219/00873* (2013.01); *B01J 23/42* (2013.01); *B82Y 30/00* (2013.01); *B01J 35/0006* (2013.01); *B81B 2201/0292* (2013.01); *B01J 23/72* (2013.01); *B22F 3/002* (2013.01); *B01J 19/0093* (2013.01); *B01J 2219/00835* (2013.01); *B01J 2219/00846* (2013.01); *B01J 2219/00853* (2013.01); *B82Y 15/00* (2013.01); *B81C 99/0085* (2013.01); *B22F 1/0025* (2013.01); *Y10S 977/762* (2013.01)
USPC ........................................... 428/573; 977/762

(58) Field of Classification Search
USPC ....................................................... 428/573
See application file for complete search history.

(56) References Cited

U.S. PATENT DOCUMENTS 5,449,917 A 9/1995 Clements
5,911,863 A 6/1999 Vetter et al.
(Continued)

FOREIGN PATENT DOCUMENTS

DE 10 2008 015 10/2009
EP 1884578 A1 2/2008
(Continued)

OTHER PUBLICATIONS

Lui J., et al: Electrochemical fabrication of single-crystalline . . . Nanotechnology, IOP, Bristol, GB, Bd. 17, Nr. 8, Apr. 28, 2006 Seiten 1922-1926 XP 020104660.
(Continued)

*Primary Examiner* — Mark Ruthkosky
*Assistant Examiner* — Ian Rummel
(74) *Attorney, Agent, or Firm* — Reising Ethington PC

(57) ABSTRACT

The invention concerns the production of segmented nanowires and components having said segmented nanowires.
For the production of the nanowire structural element, a template based process is used preferably, wherein the electrochemical deposition of the nanowires in nanopores is carried out. In this manner, numerous nanowires are created in the template foil.
For the electrochemical deposition of the nanowires, a reversed pulse procedure with an alternating sequence consisting of cathodic deposition pulses and anodic counterpulses is carried out. By this means, segmented nanowires can be produced.

14 Claims, 11 Drawing Sheets

Figure 1:
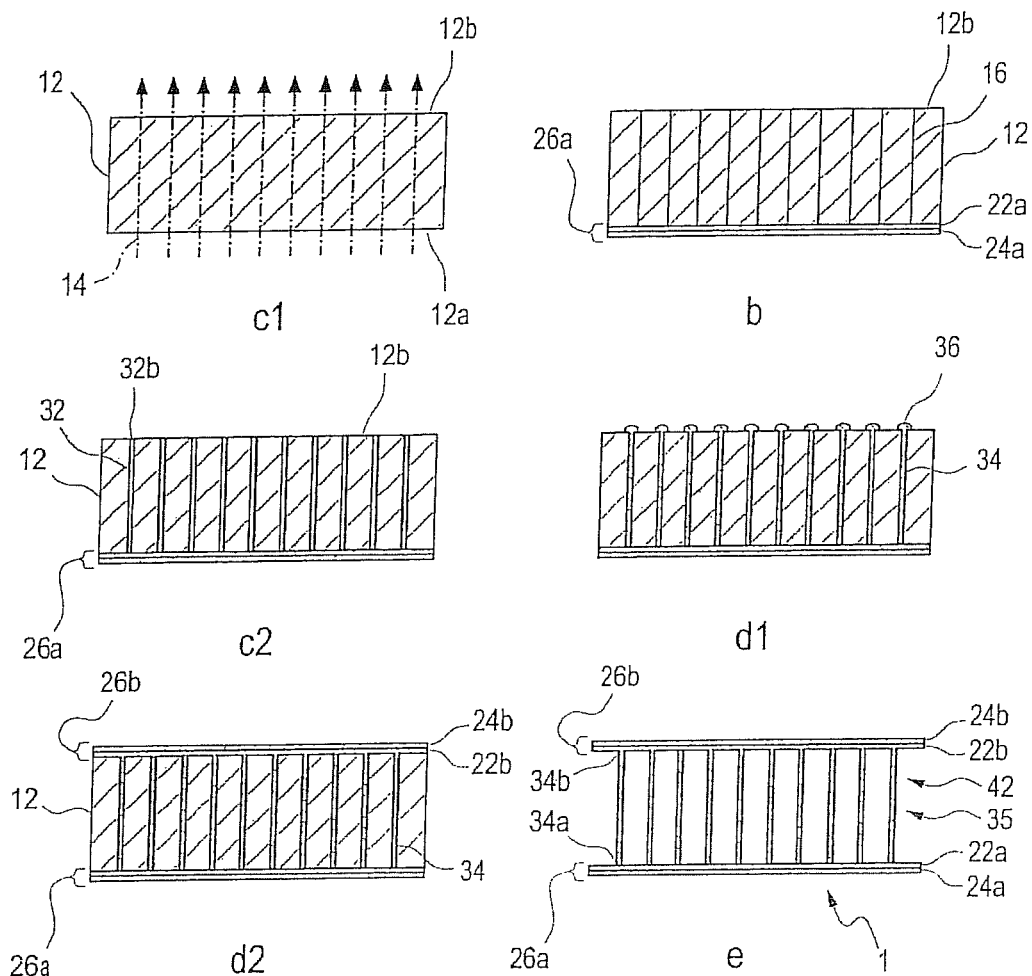

(51) Int. Cl.
| | |
|---|---|
| C25D 1/08 | (2006.01) |
| C25D 1/00 | (2006.01) |
| B01J 23/42 | (2006.01) |
| B82Y 30/00 | (2011.01) |
| B01J 35/00 | (2006.01) |
| B01J 23/72 | (2006.01) |
| B22F 3/00 | (2006.01) |
| B01J 19/00 | (2006.01) |
| B82Y 15/00 | (2011.01) |
| B81C 99/00 | (2010.01) |
| B22F 1/00 | (2006.01) |
| C25D 5/18 | (2006.01) |

(56) References Cited

U.S. PATENT DOCUMENTS

| | | | |
|---|---|---|---|
| 6,328,342 | B1 | 12/2001 | Belousov et al. |
| 2005/0230353 | A1 | 10/2005 | Danziger |
| 2006/0124467 | A1 | 6/2006 | Ho et al. |
| 2006/0134392 | A1 | 6/2006 | Hantschel et al. |
| 2007/0040191 | A1* | 2/2007 | Bezryadin et al. ............ 257/213 |
| 2007/0077429 | A1* | 4/2007 | Mirkin et al. ................. 428/402 |
| 2008/0036038 | A1 | 2/2008 | Hersee et al. |

FOREIGN PATENT DOCUMENTS

| | | |
|---|---|---|
| JP | 2004207448 A | 7/2004 |
| WO | WO 2009/115230 | 9/2009 |
| WO | WO 2010/029550 | 3/2010 |

OTHER PUBLICATIONS

Ursache Andrei, et al: Pulse Electrodeposition and Electrochemical . . . Journal of Applied Physics, American Institute of Physics N.Y. US Bd. 97, Nr.10, May 12, 2005 XP012069887.

Yi-Kun, Su, et al:Microstructure and magnetic properties of bamboo-like . . . Chemical Physics Letters, Bd. 388, Nr.4-6 Apr. 21, 2004 Seiten 406-418 XP002547633.

Li, L., et al:A new routine to fabricate Bi . . . Feb. 1, 2005, Applied Physics A; Materials Science & Processing, Springer, Berlin, DE, pp. 1053-1055 XP019336665.

Linberg M.; Hjort K:"A comprehensive study of ion track enabled high aspect ration microstructures in flexible circuit boards" Microsystem Technologies, Berlin, DE Bd. 10, 2004.

Gu, Z. et al:Three Dimensional Electrically Interconnected Nanowire Networks Formed by Diffusion Bonding Langmuir Bd. 23, Nr. 3, Dec. 23, 2006, Seiten 979-982 XP002547983.

Maurer, Florin, et al:"Preferred growth orientation of metallic fcc nanowires under direct and alternating electrodeposition conditions" Nanotechnology 18, pp. 135709 (2007).

Karim, S., et al:"Tuning the Characteristics of Electrochemically Fabricated Gold Nanowires" J.Nanosc.Nanotechnol.8, pp. 5659-5666 (2008).

Karim, S., et al:"Synthesis of gold nanowires with controlled crystallographic characteristics" App. Phys. A 84, pp. 403-407 (2006).

M. Lindeberg, et al "Interconnected Nanowire Clusters in Polyimide for Flexible Circuite and Magnetic Sensing Applications" Sensors and Actuators A, vol. 105, No. 2 150-161, 2006.

Donghai Wang, et al "A General Route to Macroscopic Hierarchical 3D Nanowire Networks" XP-002547982 Angew Chem Int Ed 2004, 43, 6169-6173.

S. Valizadeh et al., Electrochemical Synthesis of Ag/Co Multilayered Nanowires in Porous Polycarbonate Membranes, Thin Solid Films 402, pp. 262-271 (2002).

I.U. Schuchert et al., "Electrochemical Copper Deposition in Etched Ion Track Membranes", Journal of the Electrochemical Society 150 (4) pp. C189-C194 (2003).

M.E. Toimil Molares et al., "Fabrication and Contacting of Single Bi Nanowires", Nanotechnology 15, pp. S201-S207 (2004).

Changwei Xu et al., " Highly Ordered Pd Nanowire Arrays as Effective Electrocatalysts for Ethanol Oxidation in Direct Alcohol Fuel Cells", Adv. Mater. 2007, 19, pp. 4256-4259.

Japanese Office Action Re: Application No. 2011-500077 Dated: Oct. 18, 2013.

* cited by examiner

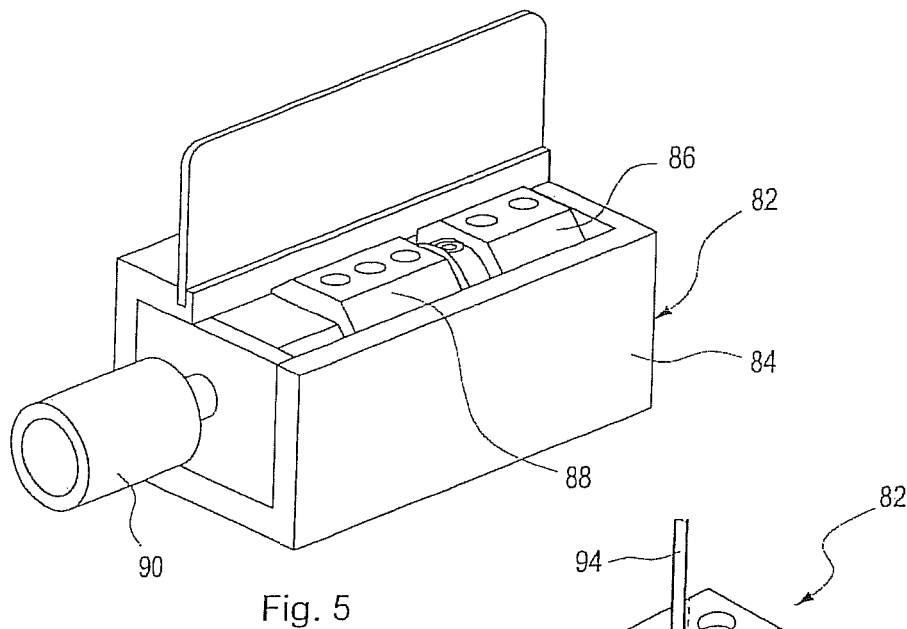
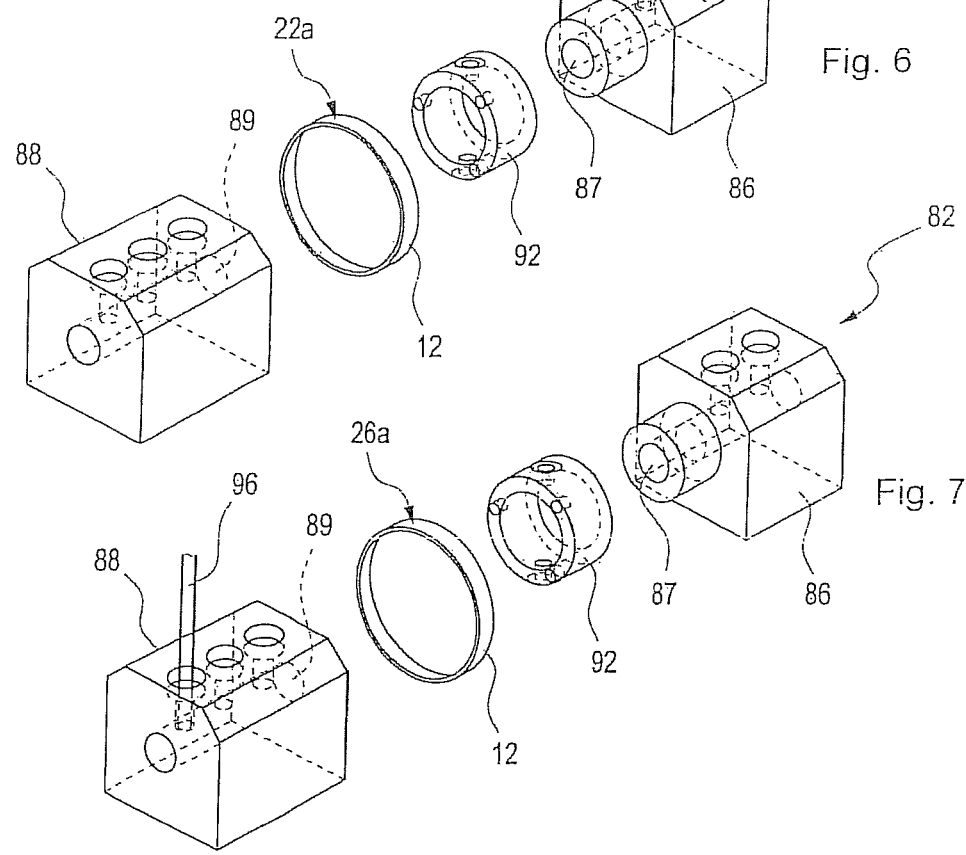

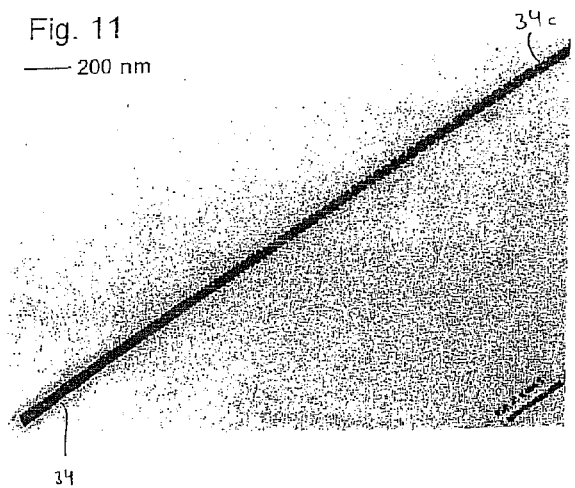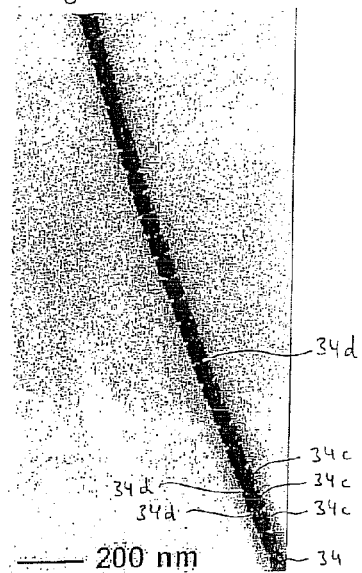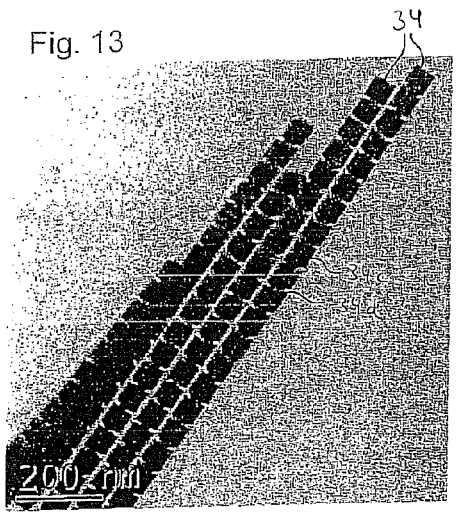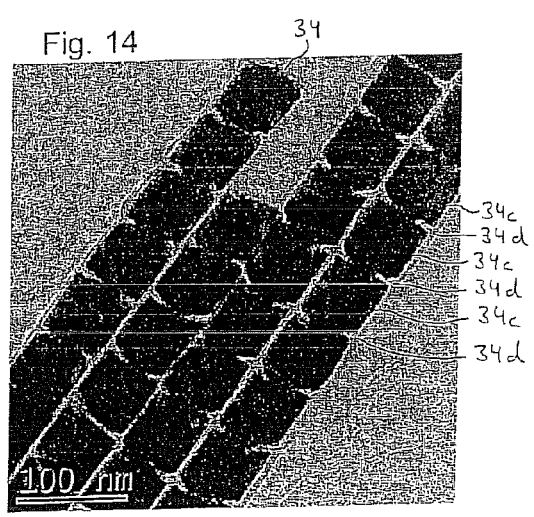

NANOWIRES AND METHOD FOR THE PRODUCTION THERE OF

FIELD OF THE INVENTION

The invention concerns nanowires with a special structure, a process for production of said as well as components made of these nanowires.

BACKGROUND OF THE INVENTION

In "Chemistry in Microstructured Reactors," Ang. Chem. Int. Ed. 2004, 43, 406-466 [: Applied Chemistry, International Edition], K. Jähnisch et al. have demonstrated the advantages that microstructured components have in chemical reactions and for analytical purposes. This has led to an increase in the importance that such systems have for chemical synthesis and analysis. In comparison to conventional reactors, these microstructures have a large surface area/volume ratio, which has a positive influence on the transference of heat as well as the process of the transportation of matter (see also: O. Wörz et al. "Micro-reactors—A New Efficient Tool for Reactor Development," Chem. Eng. Technol. 2001, 24, 138-142).

Many known reactions have been carried out in micro-structure reactors, including many catalytic reactions. For these, it is unimportant whether the reactions are liquid phase, gas phase or gas-liquid phase reactions. In order to take advantage of the potential activity of the catalyzer, the catalytic material is integrated in microstructured systems with various geometric forms. In the simplest case, the reaction material used for the construction of the micro-reactor consists in itself of the catalytically active substance (see also: M. Ficthner, "Microstructured Rhodium Catalysts for the Partial Oxidation of Methane to Syngas under Pressure," Ind. Eng. Chem. Res. 2001, 40, 3475-3483). This means however that the catalytic surface is limited to the walls of the reactor. This disadvantage is partially resolved by means of optimized catalyzer/carrier systems. For the most part, current microstructure reactors contain small particles or powder, which are incorporated in a channel.

Catalyzer filaments, wires and membranes are also used however (see also: G. Veser, "Experimental and Theoretical Investigation of $H_2$ Oxidation in a High-Temperature Catalytic Microreactor," Chem. Eng. Sci. 2001, 56, 1265-1273). Metallic nanostructures, particularly those from transition metals, are known in heterogenic catalysis due to their high ratio of surface area/mass, resulting in lower production costs (see also: R. Narayanan et al. "Catalysis with Transition Metal Nanoparticles in Colloidal Solution: Nanoparticle Shape Dependence and Stability," J. Chem. Phys. B, 2005, 109, 12633-12676).

Originally, research was concentrated on the examination of isotropic metal particles, and as a result, their catalytic characteristics have been studied at length. At present, however, many one-dimensional nanostructures have been analyzed regarding their use in heterogenic catalysis. The stabilization of these is a major problem. The incorporation of nanostructures on a carrier or storage of them in porous matter such as, e.g. Natfion is known from Z. Chen et al. "Supportless Pt and PtPd Nanotubes as Electrocatalysts for Oxygen-Reduction Reactions," Ang. Chem. 2007, 119, p. 4138-4141, which leads however directly to a decrease in the utilizable catalyzer surface area. Furthermore, it must be noted that the catalytic activity is dependent on the distribution of the catalyzer material due to the diffusion processes. Accordingly, the nanoparticles significantly increase the surface area/volume ratio, but long-term stability of such reactors is relatively limited due to the following:

1. Loss of contact between nanoparticles due to corrosion of the carrier.
2. Dissolving and renewed deposition or Ostwald ripening.
3. Aggregation of the nanoparticles in order to minimize the surface energy.
4. Dissolving of the nanoparticles and migration of the dissolvable ions.

Parallel wire and tube structures have already been used as glucose sensors (J. H. Yuan et al., "Highly Ordered Platinum-Nanotubule Arrays for Amperometric Glucose Sensing," Adv. Funct. Mater. 2005, 15, 803), as electrocatalysts, for example, in alcohol oxidation (H. Wang et al., "Pd. Nanowire Arrays as Electrocatalysts for Ethanol Electrooxidation," Electrochem. Commun. 2007, 9, 1212-1216) and for hydrogen peroxide reduction (H. M. Zhang et al., "Novel Electrocatalytic Activity in Layered Ni-Cu Nanowire Arrays," Chem. Commun. 2003, 3022). Nielsch et al. have reported in "Uniform Nickel Deposition into Ordered Alumina Pores by Pulsed Electrodeposition," Adv. Mater. 2000, 12, 582-586, that pulsed deposition is used for deposition of thin metallic foils.

All in all, there is still a great deal of potential for innovation in the field of nanotechnology.

GENERAL DESCRIPTION OF THE INVENTION

The invention has the object of providing nanowires, or respectively, a nanowire structural element with a large specific surface area.

A further object of the invention is to provide nanowires, or respectively, a nanowire structural element which may be used in a variety of ways.

The object of the invention is achieved by means of the object of the independent claims. Advantageous embodiments of the invention are defined in the dependent claims.

In accordance with the invention, numerous nanowires are produced using a template based process. For this purpose, a template is prepared having numerous nanopores which permeate the template, in particular, a template foil, and having a cathode layer on a first side of the template.

For this, a cathode layer, preferably a metallic layer, is depositioned onto a first side of the template foil. The cathode layer can be applied through deposition as a single unit, e.g. through PVD, vaporization or sputtering. Preferably, however, the cathode layer is generated in at least two layers. For this purpose, a first partial layer is depositioned, e.g. by means of PVD, sputtering or vaporization, and said first partial layer is then reinforced with a second partial layer by means of electrochemical deposition, wherein, as the case may be, a different material is used. For example, first a thin metallic layer, e.g. gold, is applied through sputtering, and subsequently this gold layer is electrochemically reinforced, for example, by a copper layer. This has the advantage that first a relatively thin layer can be applied through sputtering, which is more economical.

Ideally, the template permeated with nanopores, which may be a conventional synthetic foil, in particular a polymer foil, is produced using high-energy radiation, in particular, irradiation with high-energy ions. For example, a polycarbonate foil is irradiated with ions having an energy of a few to a few hundred MeV/u. For this, the energy of the ions is selected such that they fully penetrate the template foil. Accordingly, the energy of the ions is dependent on the thickness of the template foil, and is selected accordingly. High-energy ion beams of this type are, for example, available in the accelerator facility of the Gesellschaft fur Schwerionenforschung mbH [: Center for Heavy Ion Research; abbreviated: GSI] in Darmstadt. As a result of the irradiation a large number of latent tracks permeate the template foil. The tracks thereby indicate that the molecular structure, i.e. polymer structure of the foil is corrupted along the trajectory of each irradiation ion. These tracks are referred to as "latent tracks." The corruption is greatest at the core of the track, and is expressed as $1/r^2$. Through etching, the material having a corrupted molecular structure can be removed from the track, thus etching the latent track into an open channel. In this manner, channels can be produced having a diameter of a little as a few nanometers, and said channels are referred to as nanopores. The latent tracks, and thereby the subsequently generated nanopores are stochastically distributed in relation to the plane of the template surface area.

Subsequently, nanowires are depositioned or grown from an electroconductive material, in particular, metal, in the nanopores by means of electrochemical deposition, wherein the nanowires within the nanopores develop on the cathode layer on a first side of the template. The cathode layer is depositioned onto the template foil prior to the deposition of the nanowires in the nanopores. This can be carried out prior to the ion irradiation, between the ion irradiation and the etching which generates the nanopores, or after the etching which generates the nanopores.

With this type of nanowire production, the nanopores are filled through electrochemical deposition, starting at the inner side of the cathode layer, wherein the nanowires develop in the nanopores. The development process of the nanowires starts at the cathode layer, and the nanowires grow inside the nanopores from the cathode layer to the opposite side of the template foil. For this, the dielectric template foil, which is permeated with nanopores and electroconductively coated on one side is placed in an electrochemical deposition device. By means of electrochemical deposition of metal ions, the nanowires are depositioned in the nanopores, wherein the metal nanowires within the nanopores develop, in particular, directly on the cathode layer, and are thereby integrally formed with and thereby firmly secured to the cathode layer.

A process of this sort for the creation of nanowires is basically known, and has been demonstrated, for example, in the "Controlled Fabrication of Poly- and Single-Crystalline Bismuth Nanowires" by T. W. Cornelius et al., Nanotechnology 2005, 16, p. 246-249; and in the dissertation by Thomas Walter Cornelius, GSI, 2006; Florian Maurer, GSI, 2007, as well as by Shafqat Karim, GSI, 2007, which are hereby incorporated as references. With this process however, only homogenous nanowires are produced.

The inventors have found however, that specially structured nanowires can be produced if the electrochemical deposition is pulsed with the appropriate parameters, more precisely, by using reversed pulse deposition. With reversed pulse deposition, an alternating sequence of cathodic deposition pulses and anodic deposition pulses is applied to the template foil, or respectively, the cathode layer. During the cathodic deposition pulse, a negative voltage occurs at the cathode layer in relation to the anode, such that during the cathodic deposition pulses the nanowires develop in the nanopores, in each case of a length dependent on the duration of the respective cathodic deposition pulses and a first diameter defined by the diameter of the nanopores. During the cathodic deposition pulse, the nanopores in the corresponding segment are filled radially in their entirety. Time intervals are provided between each of the cathodic deposition pulses in which, with reversed pulse deposition, an counter-voltage, or respectively, an anodic counter-pulse is applied. It is clear to the person skilled in the art that it makes sense to use the terms "cathode layer" and "anode" even though during the counter-pulse the cathode layer is given a positive charge, and the anode, a negative charge. It has been shown, surprisingly, that during the anodic counter-pulse, the development of the nanowires is apparently not arrested, but rather, segments of the nanowires with smaller diameters, which do not completely fill the nanopores radially, but rather, are smaller, are generated. Thus, during the anodic counter-pulses between the cathodic deposition pulses, the nanowires develop respectively, at a length dependent on the duration of the respective anodic counter-pulses and a second diameter in the nanopores, wherein the second diameter is smaller than the first diameter. By this means, therefore, segmented nanowires, with an alternating series of thicker and thinner segments along the length of the nanowires, can be generated. Subsequently, the template foil can be dissolved and removed, using the appropriate solvent with a polymer foil, thus exposing the segmented nanowires.

It is assumed that the formation of segments is successful when the anodic counter-pulses establish a positive current flow away from the cathode layer. The point at which there is no current flow between the cathode layer and the anode is referred to as equilibrium voltage. The equilibrium voltage is dependent on, among other factors, material and electrolyte concentrations, and, where applicable, even dependent on temperature and can be adjusted by the person skilled in the art for any deposition system.

The cathodic deposition pulse is understood here to be a voltage pulse wherein voltage in relation to the anode is applied to the cathode layer, which is negative to a greater degree than the equilibrium voltage, in order to obtain a positive current flow from the anode towards the cathode layer.

The anodic counter-pulse is understood here to be a voltage pulse wherein a voltage in relation to the anode is applied to the cathode layer, which is positive to a greater degree than the equilibrium voltage, in order to obtain a positive current flow from the cathode layer towards the anode.

With the deposition parameters used in the embodiment, the equilibrium voltage of the cathode layer in relation to the anode is approx. −400 mV, such that with a voltage of +400 applied to the cathode layer, in relation to the cathode, an anodic counter-pulse of a relative voltage of +800 mV is obtained relative to the equilibrium voltage.

Preferably, the anodic counter-pulses have a certain positive minimal voltage relative to the equilibrium voltage in order to obtain the desired effect. The positive relative voltage to the cathode layer relative to the equilibrium voltage therefore is preferably at least +100 mV, more preferably at least +400 mV, and particularly preferable is +800 mV ±400 mV. At an equilibrium voltage between the cathode layer and the anode of −400 mV this means there must be an absolute voltage which is at least positive to a greater degree than −300 mV, more preferably positive to a greater degree than 0 mV, and particularly preferable is +400 mV ±400 mV.

Accordingly, segmented nanowires can be produced using the process described above, wherein first segments with a first diameter and second segments with a second diameter alternate, wherein the first diameter is greater than the second diameter. In other words, there are two separated first segments with the larger diameters firmly connected to each other by a second segment with a smaller diameter located between them. Thus, the first segments shall be referred to as main segments in the following and the second segments as connecting segments, wherein the main segments and the connecting segments are made of the same material.

The main segments and the connecting segments are integrally connected due to the deposition procedure; they form a unified nanowire of electrochemically formed material. The main segments are connected to each other by the connecting segments like pearls on a chain of pearls.

Advantageously, the surface area of the segmented nanowires is larger than the surface area of homogenous nanowires having a consistent diameter. Further advantages are specific to the applications.

The specific length of the first segments is determined via the duration period of the cathodic deposition pulse. The specific length of the second segments is determined via the duration period of the time intervals. In particular, the length of the first and second segments can be determined by the respective durations of the cathodic deposition pulses and the time intervals independently of one another. Accordingly, it is possible to select a predetermined length of the first and second segments respectively. For this, the duration of the cathodic deposition pulse and the duration of the time interval are adjusted accordingly in order to obtain the selected, and thereby predetermined, respective lengths of the first and second segments.

The first and second segments preferably have different lengths. It is preferred thereby that the length of the main segment with the larger diameter is adjusted to be greater than the length of the connecting segments with the smaller diameter. For this, the duration of the anodic counter-pulse is selected such that it is shorter than the duration of the cathodic deposition pulse. A cathodic deposition pulse duration which is less than 60 seconds is preferred, preferably less than 20 seconds, and particularly preferred is in the range of 1-5 seconds. The duration of the anodic counter-pulse is preferably shorter than the cathodic deposition pulse by a factor in the range of 5-1.5. The anodic counter-pulses preferably have a duration of 0.1-5 seconds, particularly preferred is 0.3-3 seconds. The duration of the cathodic deposition pulse and the anodic counter-pulse, however, should not be too short to ensure the development of the segments. A minimal duration of the cathodic deposition pulse and/or the anodic counter-pulse of at least 100 ms is assumed.

The nanowires which are produced consist accordingly of electrochemically developed electroconductive material, in particular, of metal or metallic compounds with an alternating sequence of numerous main segments with a larger diameter and numerous connecting segments with a smaller diameter. Thus, a segmented nanowire is referred to here. Because the length of the respective segments can be very small, e.g. in the range of a few to a few 100 nm, it is possible for a segmented nanowire to consist of more than 100, or as the case may be, more than 1,000 alternating pairs of main segments and connecting segments. In other words, the main segments and the connecting segments alternate in the lengthwise direction of the nanowire at regular intervals in nanometers such that continuously in the lengthwise direction of each nanowire, between two main segments there is always exactly one connecting segment.

Nanowires can be produced using the process of the invention wherein the length of the main segments is shorter than 100 mn. In general, it is possible to produce main segments of any length, wherein a length of less than 1,000 nm seems to be advantageous. The length of the connecting segments is preferably less than 10 mn, in order to ensure sufficient stability of the segmented nanowires.

The shape of the main segments is basically circularly cylindrical, as they take the inner form of the nanopores. It has been determined that the segmentation is better when the diameter of the nanopores is not too large. The diameter of the nanopores and thereby the diameter of the main segments is preferably less than 500 nm, particularly preferred is between a few nanometers and a few 100 nanometers. Preferably, the diameter of the main segments remains constant over the length of the nanowire.

If the pulsed voltage is adjusted such that the cathodic deposition pulse and anodic counter-pulse in the deposition device is a regular sequence with consistent pulse durations in each case, then the first and second segments in at least one section of the length of the nanowire have, in each case, a consistent length, such that the segmentation of at least a section of the length of the nanowire is consistent.

In general, with the template based process using a template foil allows for numerous nanowires to be produced at the same time. After their production, they can be separated from one another through the removal of the cathode layer such that numerous individual segmented nanowires are obtained.

It is however also advantageous to produce a stable nanowire structural element having an array of many of the segmented nanowires. This can be accomplished, for example, wherein the cathode layer remains as a substrate layer of the nanowire array and wherein each nanowire is integrally formed with the substrate layer. For this, the template foil is dissolved without removing the cathode layer first. In this case, the cathode layer serves a double purpose; on one hand it serves as an electrode for the electrochemical deposition procedure and on the other hand is serves as a stable, closed substrate or cover layer for the completed nanowire structural element, i.e. it remains as an integral component of the nanowire structural element which is to be produced, and is not removed from said. It is, however, conceivable that after the deposition of the nanowires in the nanopores, the cathode layer is removed and a new cover layer is applied.

It is also possible to produce a nanowire structural element that contains a nanowire array of segmented nanowires between two cover layers in such a manner that the nanowire array is enclosed in a sandwich-like manner between two cover layers. For this, in addition to the substrate layer, which is preferably formed by the cathode layer, a second cover layer is applied to the opposite side.

In order to obtain a stable connection between the nanowire array and the second cover layer, the electrochemical deposition procedure for the nanowires is carried out at least until caps have formed on the nanowires at the second side of the template foil. In particular, the following two possibilities are proposed for the generation of the second cover layer:

The electrochemical deposition procedure is continued after the complete filling of the nanopores, wherein caps are then formed on the nanowires on the second side of the template foil. When the electrochemical deposition procedure is continued, the caps grow together to form a surface covering layer and said surface covering layer increases in thickness as the deposition period is increased. Accordingly, one can continue the electrochemical deposition procedure wherein the nanowires are generated or grown until the second cover layer has developed completely, forming a sufficiently thick, stable surface covering layer. In this case, the nanowires and the entire second cover layer form a unified structure of electrochemically depositioned material. Hence, the partial steps (d1) and (d2) in FIG. 1 are carried out as partial steps of the same electrochemical deposition procedure with the same electroconductive material.

Alternatively, the electrochemical deposition procedure for generating the nanowires is carried out until caps have developed on the nanowires on the second side of the template foil, and the caps have at least in part merged together, but a stable second cover layer is not yet generated and the procedure is then arrested. The completion of the second cover layer is obtained first in a second separate subsequent deposition procedure, wherein a surface covering additional layer is depositioned onto the at least partially merged caps, such that the stable second cover layer then consists of the two layered arrangement consisting of the partially merged caps and the surface covering additional layer. The at least partially merged caps form thereby a first partial layer of the second cover layer, and the additional layer forms a second partial layer of the second cover layer. The separate deposition procedure can also consist of an electrochemical deposition, but it may also be a PVD process, vaporization or sputtering. Even when the separate deposition procedure is an electrochemical deposition, a different material may be used for the second partial layer than that used for the nanowires and the caps. The second partial layer is preferably electrochemically depositioned differently than the segmented nanowires using a direct current process. In this manner, the deposition period of the second cover layer can be reduced.

Accordingly, the second cover layer is partially or entirely generated through electrochemical deposition of an electroconductive material, preferably metal, on the second side of the template foil such that the second cover layer is firmly joined to the nanowires by being integrally formed with the nanowires.

Preferably, the ion irradiation is first carried out and subsequently, but before the etching, the cathode layer is applied. First after the cathode layer is applied to the template foil, the nanopores are etched from the latent ion induced tracks. In particular, therefore, the electroconductive metallic layer is applied to the template foil and this is reinforced electrochemically before the latent ion tracks are subjected to the chemical etching process. In this manner, material from the cathode layer being depositioned in the pores is avoided. As a result, an improved mechanical stability of the nanowire structural element generated thereby can be obtained. In addition, the pores are strictly cylindrical and do not taper at the two ends.

The result of this preferred embodiment is, accordingly, a nanowire structural element with a hollow chamber-like structure which includes of an array of numerous neighboring segmented nanowires and two parallel, separated, closed surface cover layers after the template foil is removed. The two cover layers in this embodiment are integral components of the nanowire structural element and are not separated from the segmented nanowires, but rather remain integrally joined to said, and more precisely are integrally joined by means of the electrochemical deposition procedure at the atomic/molecular level to each other. The hollow chamber-like structure can be envisioned as a chamber that can be open at one or more edges.

Accordingly, the nanowires extend perpendicularly between the two cover layers and the nanowires are integrally joined with their first ends to the cathode layer and with their second ends to the second cover layer such that the nanowires firmly connect the two cover layers to each other, and define a space between the two cover layers. In this manner, a stable sandwich-like nanostructure is formed with a two sided hollow chamber-like structure contained by the cover layers and permeated with the numerous columns of segmented nanowires running through said.

Furthermore, in this embodiment, that there are interconnected open spaces between the nanowires. The hollow chamber-like structure is, accordingly, open celled on the two-dimensional plane parallel to the two cover layers, such that between the two cover layers a fluid can be introduced in the two-dimensional open cell hollow chamber-like structure in order to interact with the large surface area of the segmented nanowires. In other words, a stable, free-standing nanowire structural element is formed which consists of the two closed cover layers and the nanowire array which is contained in a sandwich-like manner between the two cover layers and integrally joined to the same. This nanowire structural element with a nanowire array contained by surfaces on both sides, or respectively, a layered hollow chamber-like structure permeated by the nanowire array is ideally suited for use as, for example, a microreactor component, in particular as a microcatalyzer component for heterogeneous catalysis.

The distance between the two cover layers, or respectively, the length of the segmented nanowires is determined by the thickness of the template foil, and is ideally less than or equal to 200 µm, particularly preferred is less than or equal to 50 µm. This also applies when the nanowires are separated into single units.

There are further specific structural characteristics of the segmented nanowires generated with the production process however. Because the nanowires are developed from electrochemically depositioned material, they can have a specific crystalline structure, which can, for example be examined using X-ray diffraction.

Furthermore, due to the electrochemical deposition, the nanowires of the nanowire structural element are firmly integrally joined at both ends to the respective cover layers. Because the electrochemical deposition of the nanowires is carried out at least until the caps have developed and, if applicable, have merged, the nanowires and at least a portion of the second cover layer have merged into a single unit. This too can be structurally proven, in particular when the nanowires are merged in a single unit with the caps and said are at least partially merged together. When the deposition process wherein the nanowires are generated, after the merging of the caps, has been completed and a first partial layer of the second cover layer has been formed thereby and a second partial layer has been depositioned onto the merged caps in a separate step with modified process parameters, this can also be proven structurally. This applies not only when the cover layer consists of two partial layers of different material.

A larger aspect ratio allows for the generation of a larger active surface area of the segmented nanowires. The aspect ratio of the nanowires is therefore greater than or equal to 1:50, particularly preferred is greater than or equal to 1:100.

The surface density of the number of nanowires in a nanowire structural element is equally a measure for the active surface area and is ideally greater than or equal to $n/F=10^7$ cm$^{-2}$, particularly preferred is greater than or equal to $n/F=10^8$ cm$^{-2}$.

As a specific size for the active surface area of the nanowire structural element, the geometric specific surface area $A_v$ of the nanowires per area of the nanostructure element (surface of the cover layers) and per the length of the nanowires (height of the hollow chamber-like) may be used. The geometric specific surface area $A_v$ should be at least 1 mm$^2$/(cm$^2$ µm); preferred however is a larger value, specifically where $A_v$ is greater than or equal to 5 mm$^2$/(cm$^2$ µm), greater than or equal to 20 mm$^2$/(cm$^2$ µm) or even greater than or equal to 100 mm$^2$/(cm$^2$ µm) Where applicable, values of up to 1,000 mm$^2$/(cm$^2$ µm) may even be obtained.

In the production of the nanowires with the reversed pulse process, the nanowires have a distinct <100> texture, or respectively, a crystalline structure. With certain metals such as, for example, gold, it may be advantageous to create the smallest crystallite possible. For this a crystallite size of less than or equal 4 nm is preferred, wherein in general an average crystallite size of less than or equal to 10 nm may be advantageous.

Due to the crystalline texture, the actual size of the surface area is again larger than the geometric specific surface area $A_v$, which is based on the smooth cylindrical surface area, ideally by a factor of around 4-5.

In the preceding, the production of the template permeated by nanopores by means of so-called ion beam induced etching is described. It is however clear that other processes for the production of a template permeated by nanopores may be used, such as, for example, the anodizing of an aluminum foil.

Regarding the production of nanopore arrays in anodic aluminum oxide, reference is made to A. P. Li et al. "Hexagonal Pore Arrays with a 50-420 nm INterpore Distance formed by Self-Organization in Anodic Alumina," Journal of Applied Physics, 84-11, 1998, p. 6023-6026, and a review article by J. W. Diggle, Thomas C. Downie, and C. W. Goulding; p. 365-405 DOI: 10.1021/cr60259a005, which are hereby incorporated as references. Anodic aluminum oxide templates of this type have the particular characteristic that the nanopores are evenly arranged in the form of a hexagonal pattern.

A particularly preferred field of application for the nanowire structural elements is heterogenic catalysis. This means one or more components serve as catalytic components, particularly for microcatalyzers. For this, it is advantageous to extend a cover layer on one or more of the faces over the edge and allow it to merge with the other cover layer, i.e. the respective edge is integrally connected to the nanowire structural element. It is particularly simple to first close all of the edges and then slice off, for example, two opposite edges of the nanowire structural element at right angles to the cover layers.

A microcatalyzer ideally contains a microstructured channel system with a fluid intake and a fluid discharge and at least one nanowire structural element as a catalyzer element between the fluid intake and the fluid discharge, in order that fluid may be introduced by means of the fluid intake to the hollow chamber-like structure between the two cover layers, fed through the spaces between the nanowires and then removed by means of the discharge from the hollow chamber-like structure. In this manner, the two-dimensional open cell hollow chamber-like structure of the nanowire structural element is formed between the two cover layers of the catalytic reaction volumes and the cylindrical surfaces of the nanowire form the catalytically active surface area which interacts with the fluid within the hollow chamber-like structure. Ideally, due to deposition, the nanowires are formed significantly of (entirely of the same material), for example, platinum, in order that the catalytic element is a fully catalytic element.

In the following, the invention will be explained in detail using the embodiment examples and in reference to the illustrations, wherein identical and similar elements have the same reference symbols in part and the characteristics of different embodiments, particularly the procedures with and without cover layers, can be combined with each other.

SHORT DESCRIPTION OF THE ILLUSTRATIONS

They show:

FIG. 1 A schematic overview of the production of a nanowire structural element.

Figure 2:
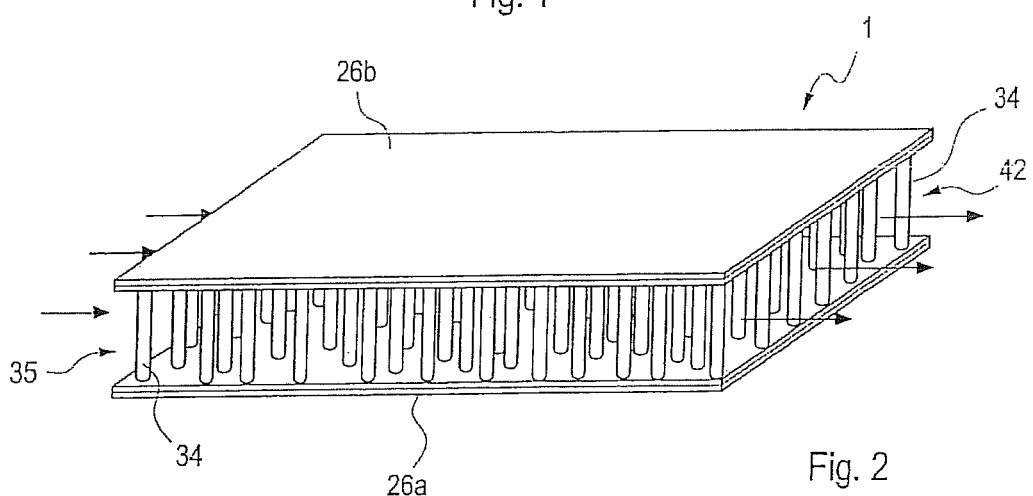

FIG. 2 A three-dimensional schematic presentation of a nanowire structural element.

Figure 3:
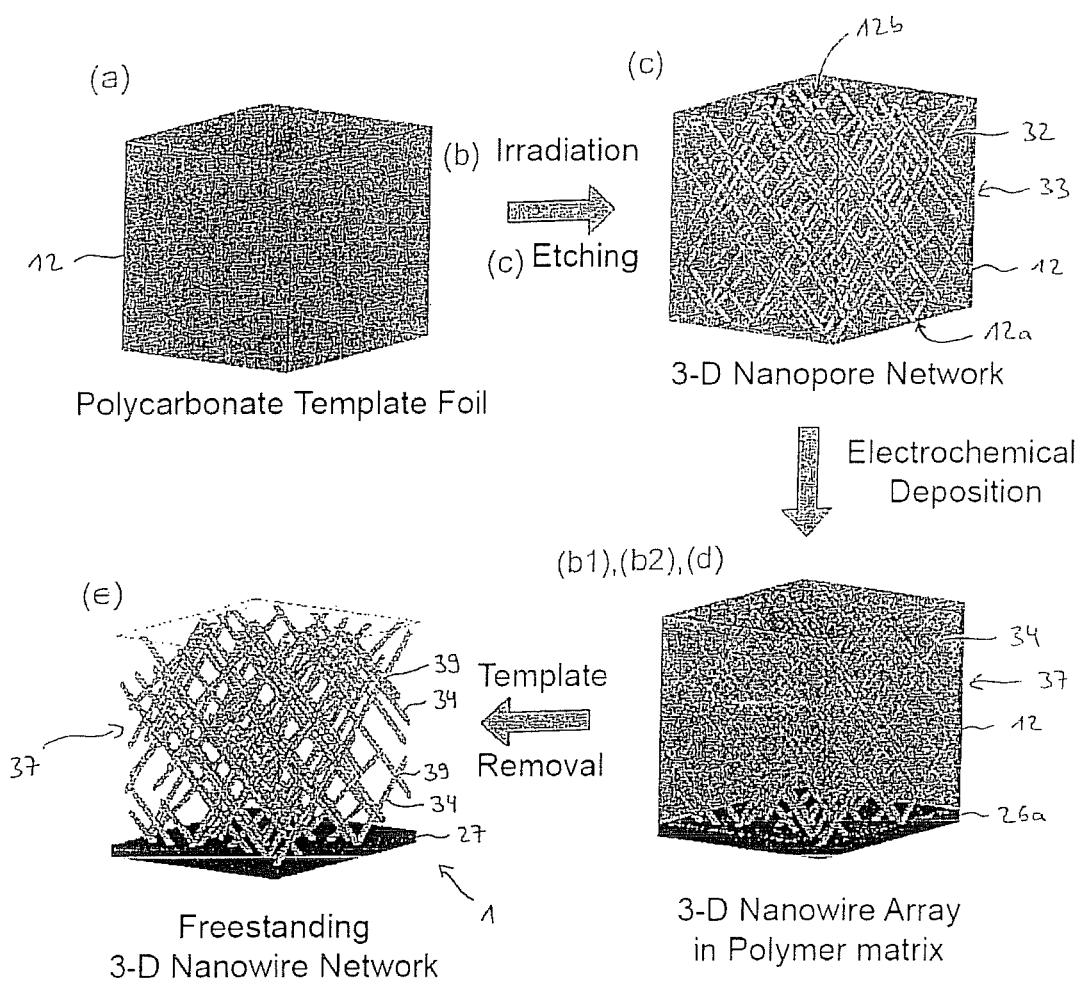

FIG. 3 A schematic overview of the production of a nanowire structural element with a three-dimensional (3-D) nanowire network.

Figure 4:
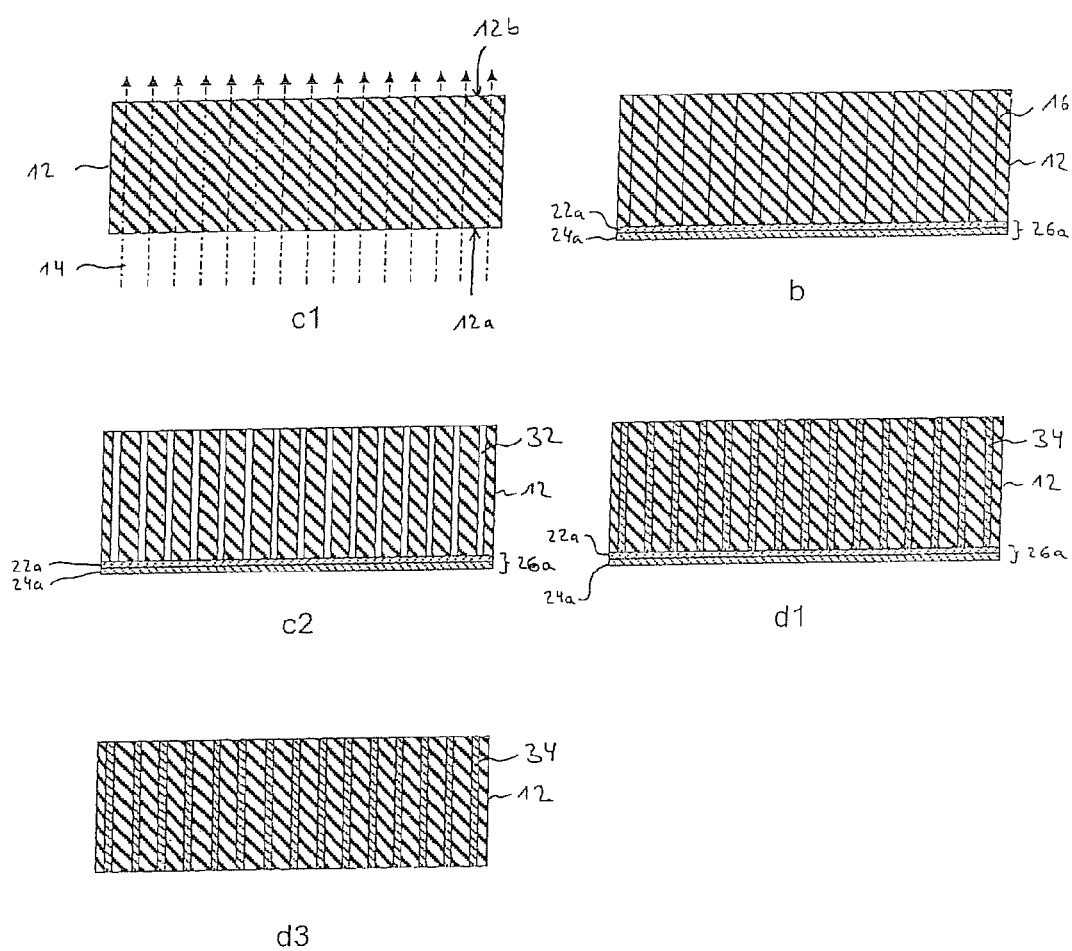

FIG. 4 A schematic overview of the production of numerous individual nanowires.

FIG. 5 A three-dimensional presentation of the deposition device used for electrochemical deposition.

FIG. 6 A three-dimensional transparent exploded image of the deposition device for reinforcing the cathode layer.

FIG. 7 A three-dimensional transparent exploded image of the deposition device for deposition of the nanowires and, if applicable, the second cover layer.

Figure 8:
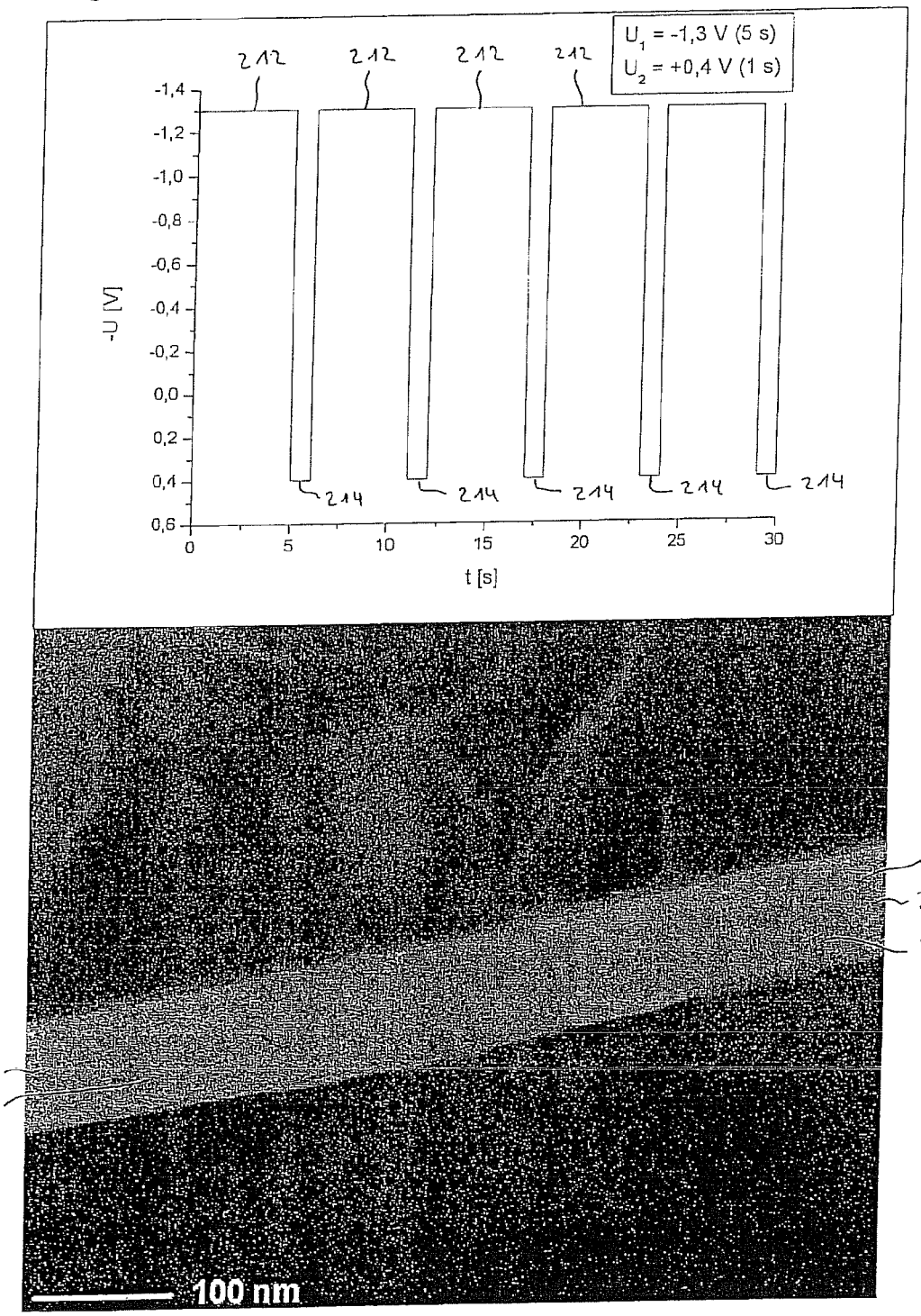

FIG. 8 A detail of the voltage flow of the reversed pulse deposition and an accompanying scanning electron microscope image (SEM) of a segmented nanowire produced thereby.

Figure 9:
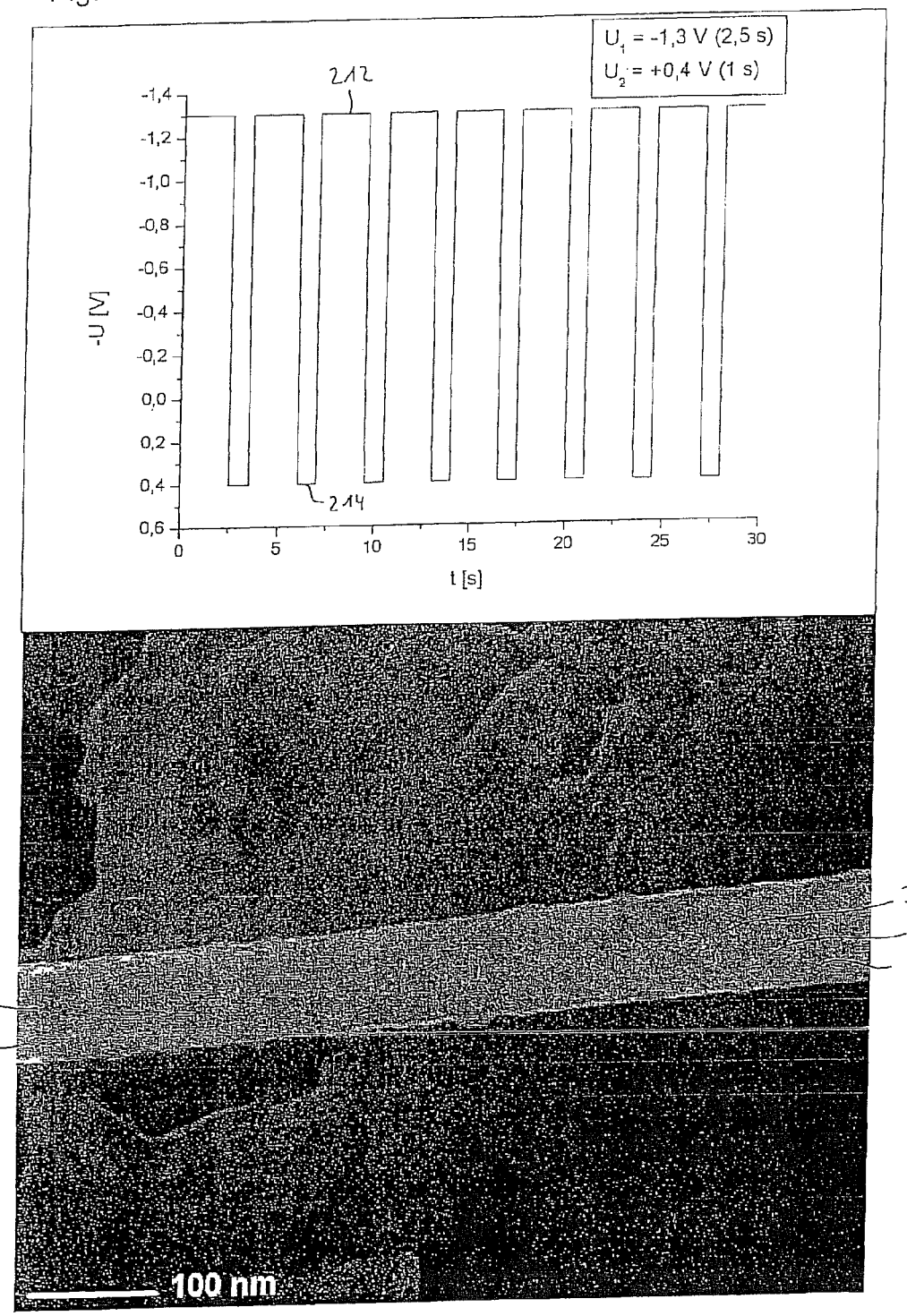

FIG. 9 The same as FIG. 8 but with a different reversed pulse voltage flow.

Figure 10:
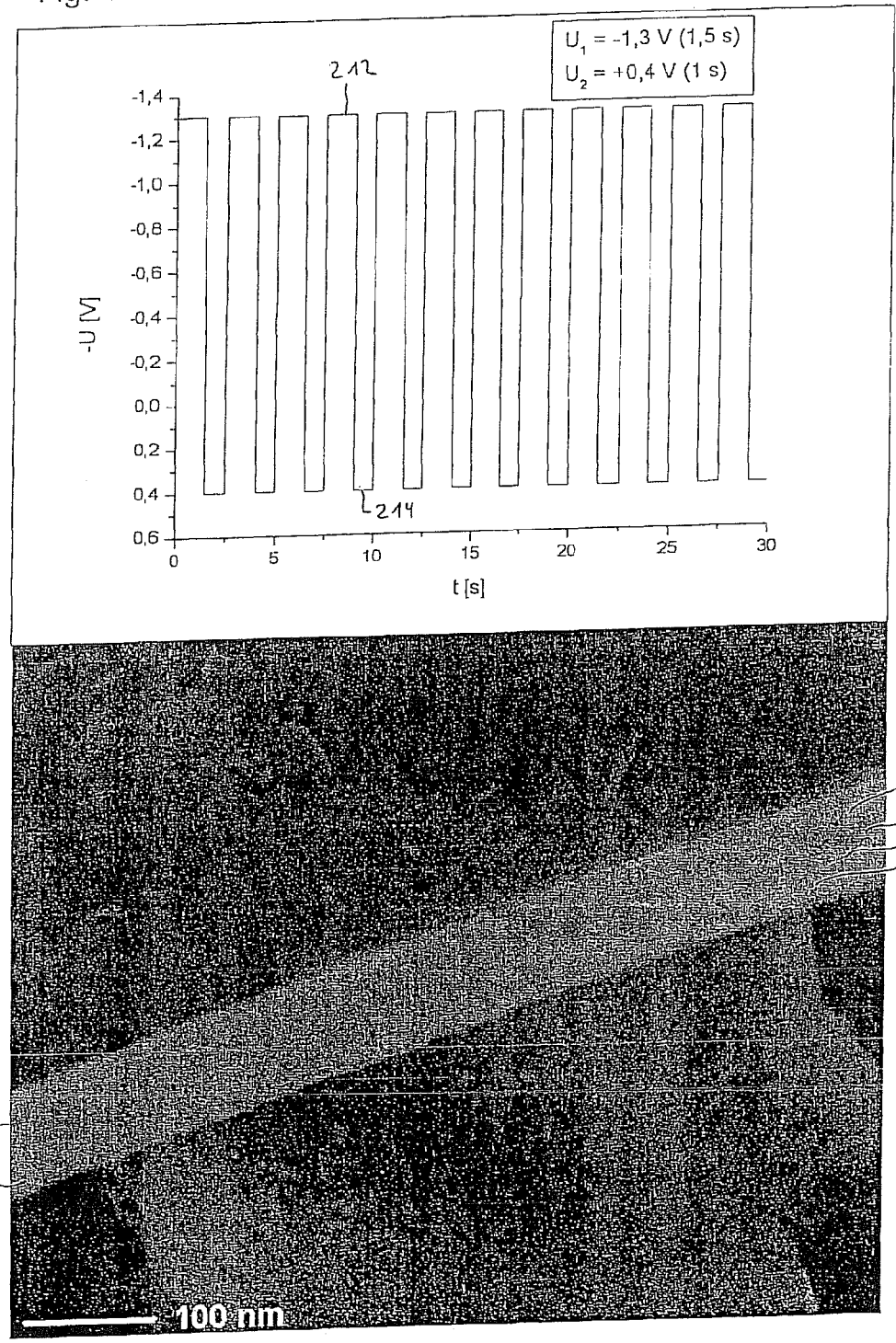

FIG. 10 The same as FIGS. 8 and 9, but with yet another reversed pulse voltage flow.

FIG. 11 A transmission electron microscope image (TEM) of a segmented nanowire.

FIG. 12 An enlarged TEM image of the segmented nanowire from FIG. 11.

FIG. 13 A TEM image of numerous segmented nanowires.

FIG. 14 An enlarged detail from FIG. 13.

Figure 15:
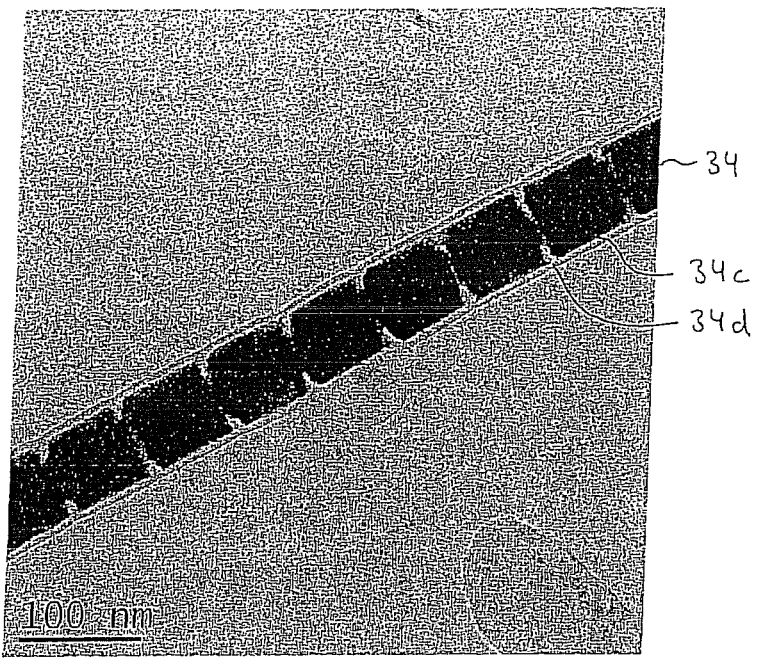

FIG. 15 A TEM image of a segmented nanowire.

Figure 16:
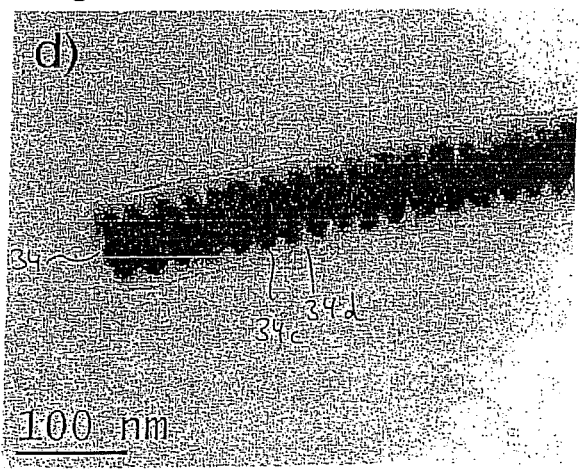
Figure 17:
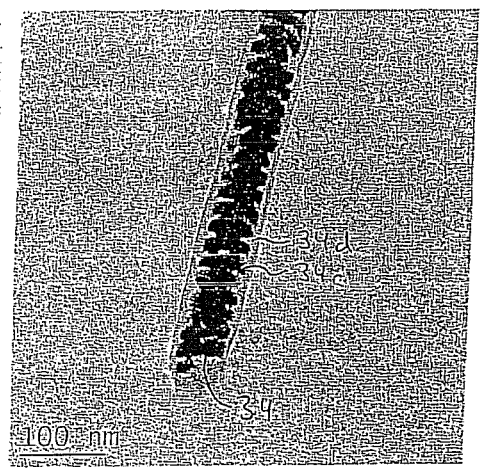

FIGS. 16 and 17 A TEM image of a segmented nanowire with shorter main segments than in FIG. 15.

Figure 18:
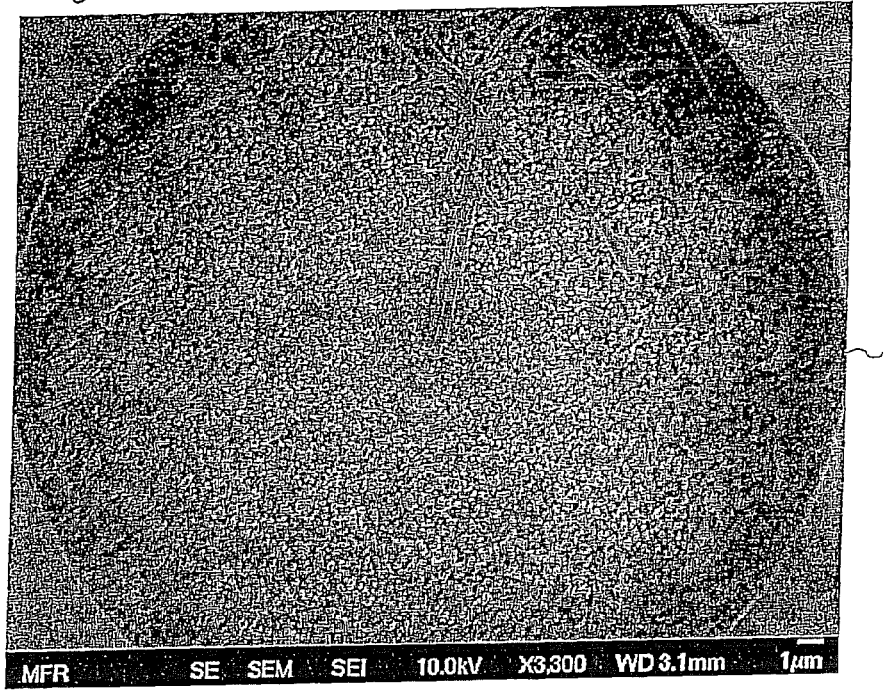

FIG. 18 An SEM image of a platinum nanowire cap produced using reverse pulse deposition.

Figure 19:
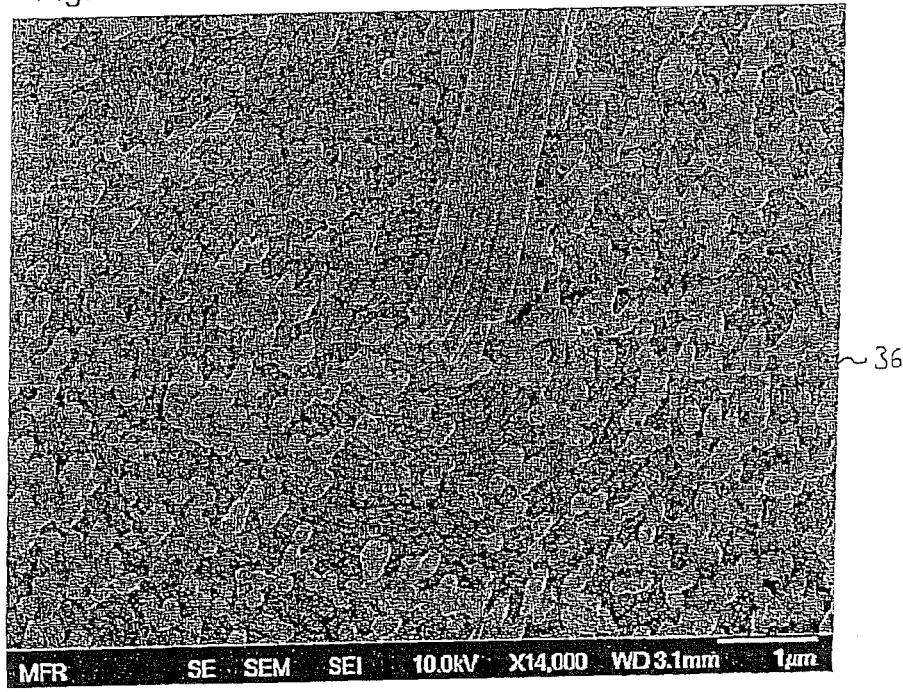

FIG. 19 An enlargement of a detail from FIG. 18.

Figure 20:
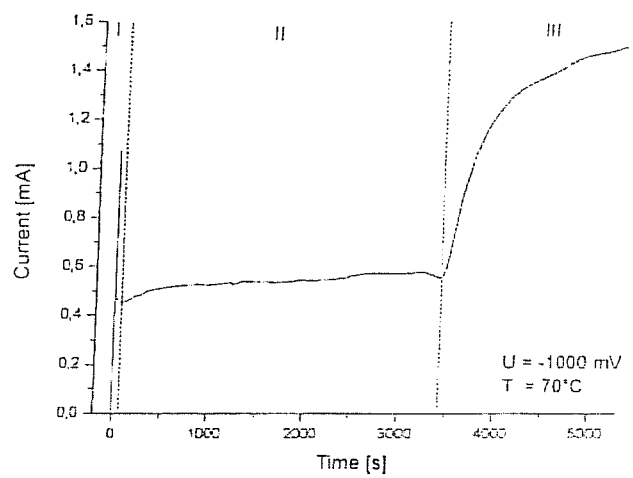

FIG. 20 Current flow in the potentiostatic production of a nanowire array.

Figure 21:
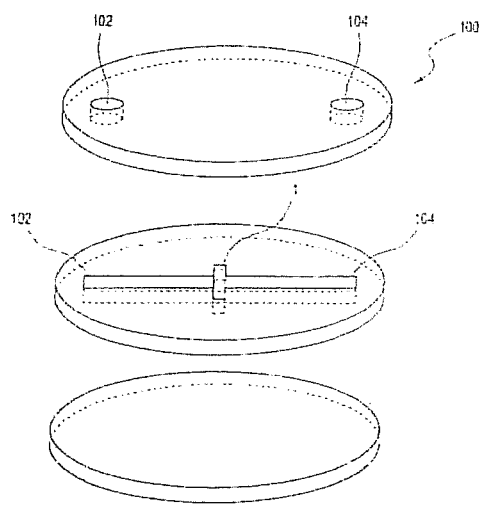

FIG. 21 A schematic exploded image of a microreactor with the nanowire structural element for flow-through operation.

Figure 22:
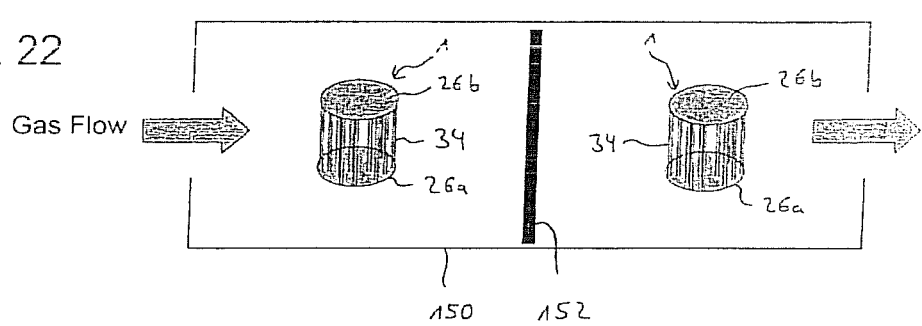

FIG. 22 A schematic presentation of a sensor element with two nanowire structural elements.

DETAILED DESCRIPTION OF THE INVENTION

EXAMPLE 1

Production of a Nanowire Structural Element with Parallel Nanowires

The production of nanowire structural elements is based on a template based process. The partial steps of the process are schematically presented in FIG. 1 as follows:

(c1) Bombardment of the template foil with ions,
(b) Application of a conductive layer,
(c2) Etching of the ion tracks to form nanopores,
(d1) Deposition of the nanowires and development of the caps,
(d2) Deposition of the second metal layer,
(e) Dissolving of the template.

Preferably the process steps are carried out in the sequence shown in FIG. 1, i.e. (c1), (b), (c2), (d1), (d2), (e). It is however possible to use a different sequence, e.g. to etch from two sides and then subsequently first apply the cathode layer partial layer ((c2) before (b)). (See, for example, FIG. 3).

With reference to FIG. 1, first a template foil 12 is bombarded with ions 14, wherein latent ion tracks 16 are generated in the substance of the template foil 12 along the trajectory (c1). The template foil 12 is a polymer foil in this example, specifically, a polycarbonate foil.

Subsequently, on the first side 12a of the template foil 12, a thin, conductive metallic layer 22a, e.g. gold, is sputtered onto said, forming a first partial layer. Subsequently, the first partial layer 22a is reinforced electrochemically with a second partial layer 24a thus forming the first cover layer 26a, which later serves as an electrode for nanowire deposition (b). For the electrochemical deposition of the second partial layer 24a, the template foil 12 is mounted in the deposition device 82 as shown in FIGS. 5-7.

Subsequently, the template foil 12 coated on one side is then removed from the deposition device 82, and the latent ion tracks 16 are chemically etched, wherein uniform nanopores 32 are created.

Alternatively, the etching process may also be carried out in the deposition device 82, in that the etching solution is placed in the appropriate cell 88, and after completion of the etching, removed from said. A removal of the template foil and the replacement of said are not necessary. The diameter of the nanopores 32 can be controlled by adjusting the etching time period (c2).

Following this, the template foil 12 prepared in this manner is placed again in the deposition device 82, and using the appropriate electrochemical process, the desired metal is depositioned in the nanopores 32 (d1). When the nanowires 34 reach the ends of the pores 32b at the second side 12b of the template foil 12, caps 36 begin to form. Under suitable conditions, the caps 36 merge together in a layer, forming a second, closed, but not yet sufficiently stable, metallic layer 22b parallel to the first cover layer or cathode layer (d2). This metallic layer, in this example, is a first partial layer 22b, on which a second metallic layer is depositioned, forming a second partial layer 24b (d2). By means of the second partial layer 24b, the caps which have merged together are embedded in a mechanically stable manner. In this way, the first and second partial layers 22b, 24b together form the second cover layer 26b.

Finally, the polymer foil 12 is dissolved in an organic solvent suited to this purpose (e). The nanowire structural element 1, produced hereby in accordance with the invention, is shown in FIG. 2. For reasons of simplicity, the segmentation of the nanowires is omitted in FIG. 2. As the SEM and TEM images show (FIGS. 8-17), the nanowires 34 produced according to the invention however, with the correct selection of the deposition parameters, as will be explained in the following, is in fact segmented. At least the inner side facing the hollow chamber-like structure 42 of the second cover layer 26b is at least partially formed hereby by means of an electrochemically depositioned layer 22b.

The template based method has the advantage that many of the parameters can be specifically manipulated. The length of the nanowires 34 is determined by the thickness of the template 12 used and ideally is 10-100 μm, particularly preferred is circa 30 μm±50%. The surface density of the nanowires 34 is determined by the irradiation and for production of the array is ideally between $1 \times 10^7$ and $1 \times 10^9$ cm$^{-2}$. The diameter D of the nanowires 34 is determined by the time period of the etching and may be from ca. 20 nm to 2000 nm. The aspect ratio may have values of up to 1000.

The thickness of the cathode layer 26a, and the second cover layer 26b is controlled through the time period of the respective electrochemical deposition, and should be thick enough that sufficient stability is obtained. The thickness of the second cover layer 26b should be at least 1 μm. Preferably, the thickness is however greater than 5 μm, e.g. between 5 μm and 10 μm. The same applies to the cathode layer 26a.

Possible materials for the nanowires are metals which are suited to electrochemical deposition. Experience has been made with the following metals: Cu, Au, Bi, Pt, Ag, Cu, Cu/Co multilayer, $Bi_2Te_3$.

On the one hand a large number of nanowires 34 with small diameters D is desired, in order to obtain a large active surface area, and on the other hand a good mechanical stability should be obtained. The optimization of this depends on the material used and is adjusted to the needs accordingly.

For nanowire structural elements 1 with platinum nanowires 34 between copper partial layers 24a, 24b, a stable construction is produced with $10^8$ wires per cm$^2$ having a diameter of 250 nm and a length of 30 μm. The aspect ratio here is 120. Such elements are suited, for example, for use as catalytic elements.

To produce the nanowire structural elements 1, as an alternative to polymer foils 12, other template foils such as hard template foils of aluminum oxide may also be implemented. The pore diameters which can be obtained here are between 10 and 200 nm. The density hereby is sufficient at ca. $6.5 \times 10^8$-$1.3 \times 10^{11}$ cm$^{-2}$. Porous aluminum oxide templates allow for the generation of uniformly arranged structures. It is also conceivable to use templates of ion track etched glasses and mica-films. With these templates, the removal of the template is achieved with hydrofluoric acid (HF), wherein the selection of the metal for the wire deposition and the metallic layers is somewhat limited.

EXAMPLE 2

Production of a Nanowire Structural Element with an Cross-Linked Nanowire Array

FIG. 3 schematically shows the production of a nanowire structural element with an interconnected nanowire array. For this, the template foil 12 is irradiated from numerous different angles with ions such that the latent tracks and later the intersecting nanopores, or respectively, the intersecting nanowires run at an angle, for example, 90°, to each other. It is to be understood that other angles are also possible.

For successive irradiation of the template foil 12 at various angles, the template foil 12 is first positioned in a corresponding jet tube at a first angle to the direction of the ion beam, e.g. in the synchrotron of the GSI, and irradiated with a predefined first ion surface density. Subsequently the template foil 12 is tilted in relation to the beam direction and again irradiated with a predefined second ion surface density. If nanowires are to be generated at more angles, the procedure is repeated for as many angles as desired. To produce a 3-dimensional network, the template foil 12 positioned at a polar angle to the beam axis is rotated around the beam axis in the azimuth plane, for example Furthermore, the process is carried out as shown in the example displayed in FIG. 1, wherein however, the second cover layer may be omitted.

The nanowire structural element 1 produced in this manner is shown schematically in FIG. 3 (e). The nanowire structural element 1 contains one, or consists of a, nanowire array 35 of intersecting merged together nanowires 34 which form an integral meshed nanowire network 37. The network 37 already has a certain inherent stability, due to the meshed structure of the merged together nanowires, without cover layers, thus being open on all sides even though cover layers of the type described, e.g. on one side (substrate layer, formed by the remaining cathode layer 26a) or on two sides forming a sandwich structure, are not ruled out as a possibility.

EXAMPLE 3

Production of Individual Nanowires

Although it is preferred that a nanowire structural element 1, as is described based on FIG. 1 or FIG. 3, it is however, basically possible as well, to produce individual segmented nanowires 34. A schematic presentation of the production steps is shown in FIG. 4. In this case, the electrochemical deposition is arrested before the development of caps begins (d1) and subsequently the cathode layer 26a is removed. This is particularly possible if the cathode layer 26a or at least the first partial layer 22a consists of a different material than the nanowires 34. The template foil 12 is subsequently dissolved in a step (e) thus causing the individual nanowires 34 to separate (not shown).

Exemplary Parameters for the Production of the Segmenting of the Nanowires

All of the examples described in the preceding are produced with segmented nanowires 34 in accordance with this invention.

For example, a 30 µm thick, a circular shaped (r=1.5 cm) polycarbonate foil 12 (Macrofol®) irradiated with heavy ions 14 having an energy of 11.1 MeV/u and a fluence of $3\times10^7$ ions/cm$^2$ is used. Prior to the application of the conductive metallic layer 22a, each side of the polymer foil 12 is irradiated for one hour with UV light, in order to increase the selectivity of the etching along the tracks 16.

A gold layer 22a is sputtered onto the first side 12a of the polymer foil 12, having a thickness of ca. 30 mn. This is reinforced by a potentiostatic deposition of copper from a CuSO$_4$ based electrolyte solution (Cupatierbad, Riedel) with a voltage of U=−500 mV, wherein a copper rod electrode serves as the anode (partial layer 24a). The deposition is stopped after 30 minutes, at which point the copper layer 24a is approx. 10 µm thick. Subsequently, etching is carried out from the untreated side 12b of the template foil 12 at 60° C. with an NaOH solution (6 M) for 25 minutes and thoroughly rinsed with deionized water, to remove residual etching solution. At this point, the nanoporous template foil 12 is mounted in the deposition device 82. The deposition of nanowires 34 is carried out at 65° C. with alkaline Pt electrolytes (Pt-OH bath, Metakem).

With reference to FIG. 8, the process of the reversed pulse deposition is used for the generation of the nanowires 34. Unless otherwise indicated, the voltage indicators refer to the voltage between the cathode layer 36a and the anode 96 from the perspective of the cathode layer 36a.

A cathodic deposition pulse with an absolute voltage of U=−1.3V for 5 seconds is followed by an anodic counter-pulse for 1 second with an absolute voltage of U=+400 mV and so on. The upper illustration shows a detail of the pulsed voltage flow, applied to the cathode layer 26a, over time. After a few tens of minutes, the deposition is stopped and the development checked. With the configuration used and a polymer foil as the template foil 12, the equilibrium voltage in this example is approx. −400 mV, such that the relative voltage of the cathodic deposition pulse is approx. −900 mV and the relative voltage of the anodic counter-pulse is approx. +800 mV, in each case calculated in relation to the equilibrium voltage. The alternating cathodic deposition pulse 212 and the anodic counter-pulse 214 are repeated numerous hundreds of times in a deposition period of a few tens of minutes, wherein FIG. 8 shows only a detail of a few pulses, 212, 214.

The segmented nanowire 34 generated with this pulse sequence can be seen in the accompanying SEM image (FIG. 8, bottom). The segmented nanowire 34 consists of a periodic alternating sequence of thicker main segments 34c and thinner connecting segments 34d. The connecting segments 34d connect in each case two neighboring main segments 34c, wherein the nanowire 34 is nonetheless developed from the same material. The connecting segments 34d can also be regarded as periodic contractions of the nanowire 34. The main segments 34c have an approx. length of 50-100 nm. The connecting segments 34d have an approx. length of 10 nm or less.

FIG. 9 shows a comparable illustration to FIG. 8, but with cathodic deposition pulses 212 shortened to 2.5 seconds. Accordingly, the main segments 34c are shorter than in FIG. 8 by half approx. The anodic counter-pulses 214 are maintained at a constant rate of 1 second.

FIG. 10 shows a comparable illustration to FIGS. 8 and 9, but with cathodic deposition pulses 212 shortened to 1.5 seconds. Accordingly, the main segments 34 c are again shorter than in FIG. 9. It can be seen that the surface of the nanowire 34 becomes larger when the sequence of the segments 34c, 34d is shortened and when the nanowire 34 contains more segments.

With the process in accordance with the invention, it is therefore possible to set a predetermined length of the rate of repetition of the segmenting wherein the duration of the cathodic deposition pulse 212 is selected accordingly. In particular, the length of the main segments 34c can be set for a specific desired length. It is therefore assumed that the length of the connecting segments 34d can also be set by means of selecting the duration of the anodic counter-pulse 214. These lengths should not, however, be selected at a size which is too large to obtain a sufficient stability of the nanowires 34. In the FIGS. 8-10 it can furthermore be seen that the segments 34c, 34d within a respective nanowire have, for the most part, a consistent length along the length of the nanowire 34, at least in the illustrated section of the nanowire 34. The diameter also remains consistent, which can be attributed to the cylindrical form of the nanopores 32.

If a second cover layer 26b is to be generated, the deposition is continued until the caps 36 have merged sufficiently to the partial layer 22b, in order that the potentiostatic deposition of a copper partial layer 24b at, for example, U=−500 mV for approx. 30 min. can be applied.

Finally, the template foil is removed, wherein the entire nanowire structural element with the template foil 12 is placed in a container with 10 ml dichloromethane for several hours. The solvent is replaced three times in order to fully remove residual polymers.

The inventors assume that the process of the segmenting can be explained as follows. The prevalent transport process, wherein the metal ions make their way to the nanopores 32, is diffusion in the electrolyte solution. For the deposition of the nanowires 34, two different types of diffusion occur that effect the lengths of the segments. The electrochemical behavior of nanoelectrodes which can be observed in the nanowires 34, is different from that of macroelectrodes. The metal ions are reduced on the electrode surfaces, and are thereby removed from the solution. In this manner, a diffusion layer forms and a concentration gradient occurs between the region without ions and the concentration in the solution. The diffusion layer grows over time in the solution. As a result, the current, limited by diffusion, decreases over time.

For short periods of time, planar diffusion in the nanochannels 32 can be assumed and the behavior can be described according to the Cottrell equation. This results in a time dependent diffusion limited current proportional to $1/t^{1/2}$ wherein t is time. With longer time periods, the diffusion layers reach from the nanopores 32 into the solution, where spherical diffusion behaviors prevail. The current there is, for all practical purposes, independent of time.

In FIG. 20, the voltage flow during a potentiostatic production of nanowire arrays 35 is illustrated. The curve can be separated into three regions. In region I, a stronger decrease of the voltage signal can be observed. Planar diffusion in the nanopores 32 is prevalent here. In region II the diffusion layer has reached the solution, and hemispherical diffusion is prevalent. Finally, the nanowires have grown out of the nanopores 32 in region III and formed caps. The electrode surface increases and planar diffusion occurs again.

The diffusion behavior during the potentiostatic production of nanowire arrays described can be applied to nanowires 34 for the electrochemical deposition of arrays with segmented nanowires using reversed pulses, if the reversed pulse length is sufficiently short, in order that an exaggerated compensation of the concentration differences does not occur and the diffusion layer does not infiltrate the solution. The pulse lengths of the cathodic deposition pulse 212 and the anodic counter-pulse are accordingly selected in a range which is sufficiently short.

If the pulse length of the cathodic deposition pulse 212 and the anodic counter-pulse 214 is maintained at a constant rate, the segment length is proportional to the diffusion current. Because the diffusion current is relatively constant after a short period, the lengths of the segments 34c, 34d should remain constant after a short deposition period. This has been shown to be true by transmission electron microscope (TEM) images. It can be clearly seen in FIG. 11 that the main segments 34c along the axis of the wire become longer at first from bottom left to top right until they obtain consistent lengths after approx. 2 μm. A TEM image in accordance with FIG. 12 from the middle of the wire of the same nanowire 34 displays segments with the same lengths. The illustrated platinum wire 34 is produced with cathodic deposition pulses of 5 seconds at an absolute voltage of U=1.3 V and anodic counter-pulses of U=0.4 V for 1 second, as shown in FIG. 8.

The relatively shorter segments and increasing lengths along the axis of the wire at the beginning of the deposition can be explained in that at first the diffusion layer is very short and as a result, only a small volume of metal ions are present in the nanochannels 32 when the pulse length of the cathodic deposition pulse 212 can be delivered and reduced. The diffusion layer infiltrates the solution and the number of electrochemically active species which enter the diffusion zone increases. The diffusion current increases until, due to the hemispherical diffusion at the pore openings, it becomes independent of time for all practical purposes. At this point, the length of the main segments 34c hardly changes. When a nanowire 34 reaches the end of its nanopore 32, a hemispherical cap 36 is formed. The neighboring nanowires 34 which have not yet reached pore ends grow significantly more slowly because nearly all of the substance transport goes to the newly developed cap 36. As the cap 36 grows larger, the planar portion of the diffusion to the cap surface becomes larger and the hemispherical portion of the diffusion to the cap surface becomes smaller. As a result, the diffusion current density decreases while the entire current increases due to the increasing size of the electrode surface. This transition to caps 36 produced with reversed pulse deposition is noticeable. In FIGS. 18 and 19 a nanowire cap 36 may be observed during the development on the side facing the template 12. The ring-like structures occur as a result of the pulsed process. The cap sections grow outwards from the middle. Each ring segment corresponds to a pair of cathodic deposition pulses 212 and anodic counter-pulses 214. The sections become thinner at the edges with decreasing diffusion current. In this direction, the entire surface increases with the entire current. Accordingly, the caps 36 are also segmented in rings.

The formation of segments is also ensured through a sufficiently positive anodic counter-pulse 214. It is assumed that during the anodic counter-pulse 214 a transport process takes place in the nanopores 32 from the end of the developing nanowire to the pore end. This transport process is faster on the walls of the nanochannels, wherein a deviation from the cylindrical form of the segments occurs, wherein a contraction occurs respectively forming a thinner connecting segment 34d respectively. It is assumed that in this case the charge to the walls of the pores and the pH value of the electrolyte solution play a role. The electrolyte solution is preferably alkaline (pH>7). The segments extend into the pore "deeper" at the middle than at the edges. This can be observed in the TEM image (e.g. FIG. 15). It should also be noted here that there is a clear contraction in each case between the individual main segments 34c, resulting in neighboring main segments 34c being joined by connecting segments 34d, wherein the connecting segments 34d have a smaller diameter, which can be clearly seen in FIGS. 13-17. Segmented nanowires of this type are very interesting, because they have a larger surface area than homogeneous cylindrical wires and should display a lower conductivity, or respectively, a higher resistance.

By means of the examination of the nanowires 34 segmented in this manner, the diffusion currents and thereby the diffusion behavior can be readily examined accordingly. The clear structuring after each pulse allows for statements regarding the temporal progress of the development and makes these somewhat one-dimensional nanostructures a model system for electrochemical depositions in materials with high aspect ratios in regard to transport processes.

Presumably, the prevailing transport processes play a role in the formation of the segments 34c, 34d during the reversed pulse deposition in the nanochannels 32. It has been shown that for the formation of the segments an alkaline electrolyte solution (pH>7) is suited for the electrochemical deposition of the nanowires 34 in combination with a polymer foil 12, in particular a polycarbonate foil, used as a template foil. The electrolyte solution is preferably highly alkaline (pH>11).

It is presumed that due to negative surface charges on the polycarbonate templates used, as occurs, for example, with glass and quartz surfaces, with a sufficiently positive pH value an electric double layer is formed. The electrostatic forces result in a preferred accumulation of cations from the electrolyte solution on the surface—a double layer is formed. This consists of a rigid (stellar layer) and a dynamic diffused border layer. Like a star, a potential is formed which can be separated into two regions. In the rigid border layer, a linear potential decrease is observed, and in the diffused layer an exponential potential decrease (zeta-potential) is observed. If an electric field is applied along a double capillary with a double layer, then the dynamic cations in the diffusion layer are drawn in the direction of the cathode. Because the solvation shell of the ions is carried along and the diffused layers come quite close, the entire electrolyte solution is moved in thin capillaries. The flow of the entire solution in an electric field is referred to as the electroosmotic flow (EOF).

In the nanopores, the electric double layer is comparable in its dimensions to the diameter of the nanopore 32, which is why fluids and ions have stronger interactive forces with the walls.

Transport phenomena in nanopores 32 (diameter<1,000 nm or even<500 nm) are distinguished between those in micrometer channels and those in millimeter channels. Because large regions of the nanopores 32 can be coated with electric double layers which form on the walls, powerful effects to the flow rate of the fluid and transport of ions can be expected in that the flow profile and the spatial distribution of ions is altered. With very small diameters, such as those present with the nanowires 34 produced here, the flow profile deviates from a flat shape, and becomes parabolic. It becomes increasingly pointed as the diameter is reduced. Therefore, at least some of the parameters:

Material of the template foil,
Relative voltage of the cathodic deposition pulse in relation to the equilibrium voltage,
Relative voltage of the anodic counter-pulse in relation to the equilibrium voltage,
Diameter of the nanopores 32
pH value of the electrolyte solution, are selected such that an electric double layer is formed in the nanopores during the deposition of the nanowires 34 in the nanopores 32, and in particular, such that the dimensions of the electric double layer in the nanopores 32 are in the same size range as the diameter of the nanopores 32.

A parabolic shape can also be seen in the segmented nanowires 34. The main segments 34c are only connected to the connecting segments 34d in the middle because, due to the parabolic flow profile, the ions first make contact with the momentary cathode at this point which is respectively formed and reduced by the immediately preceding segment.

It is important to have a high pH value to obtain a large zeta-potential and thereby a large EOF. The pH value of the Pt electrolyte solution used is approx. pH=13. In addition, the EOF decreases as the electrolyte concentration decreases. Temperature may also have an effect, as this may alter the viscosity of the solution.

With reversed pulse deposition, the ion transport for each segment is carried out anew in the direction of the preceding depositioned segment, and the corresponding profile is formed anew. Because the polarity of the relative voltage in relation to the equilibrium voltage is reversed with each pulse, the transport direction changes with each pulse.

Construction for the Electrochemical Deposition

With reference again to the FIGS. 5-7 the electrochemical deposition of the wires 34 in all embodiments is carried out using the deposition device 82 which shown in FIG. 5. It consists of a metal housing 84, in which the metal sled containing one of the two electrolysis cells 86, 88 can be inserted. Due to the good heat transfer properties of metal, it is possible to temper the deposition device by controlled external heating.

The electrolysis cells 86, 88 made of PCTFE have on their two facing sides, in each case, circular openings 87, 89 of the same size and can be pressed together firmly with a hand-turned screw. A copper ring 92 between the two electrolysis cells 86, 88 serves as a cathode, or respectively, to establish contact with the first cover layer for the electrochemical deposition.

With reference to FIG. 6, for electrochemical reinforcement of the partial layer 22a, the ion track etched template foil 12 is mounted between the two electrolysis cells 86, 88 such that the partial layer 22a, in this case, the sputtered gold layer 22a, establishes a good contact with the ring shaped copper electrode 92. On both sides of the copper ring being used as a cathode, electrolytes are injected into the electrolysis cells. The electrochemical reinforcement of the gold layer 22a on the first cover layer 26a is carried out with a first anode 94, which is placed in the electrolysis cell 86 facing the partial layer 22a, and an external power source with a control device.

After removing the template foil 12 and etching the nanopores 32 outside of the deposition device 82, the template foil 12 is placed again in the deposition device 82.

With reference to FIG. 7, the template foil 12 which has been coated on one side and made porous is again placed in the deposition device 82 as in FIG. 6 for electrochemical deposition of the nanowires 34, and where applicable, the caps 36 and, where applicable, the completion of the second cover layer 26b, such that the first cover layer 26a makes contact with the ring electrode 92. At this point, deposition is carried out on the second side 12b of the template foil 12 with a second anode 96 located in the electrolysis cell 88 on the side away from the first cover layer 26a. This deposition procedure is carried out for the generation of segmented nanowires 34, as described above, using the reversed pulse process.

Structural Characteristics of the Nanowires

In the framework of the invention the structural characteristics of the nanowires 34 made of different materials is also studied. With electrochemically depositioned material it is possible, for example, to control the size of the crystallite. This affects the mechanical stability, the thermal and electrical transference characteristics as well as the surface area and thereby also the catalytic activity. Many characteristics can thereby be strategically influenced.

In particular, the structure of the nanowires 34 is studied using X-ray diffraction. For this, the texture as a function of the electrochemical deposition is analyzed. Should one examine the nanowires 34 produced using reversed pulse deposition, they display a clear <100> texture, wherein the texture coefficient $TC_{100}$ is 4.16. The crystallites display accordingly a preferred orientation, wherein the degree of the alignment is 83%. An alignment of at least 50% in this case is advantageous. Where applicable, the nanowires produced in accordance with the invention therefore display a crystallite structure.

Applications

As a catalyzer it is possible to connect a series of numerous nanowire structural elements 1 according to the invention. Based on measurements, the nanowire structural element 1 is suited individually for application in microstructured systems having three-dimensional structures wherein the internal measurement is less than 1 mm and for the most part lies between ten and a few hundred micrometers.

FIG. 21 is a schematic illustration of a microcatalyzer 100, in which a nanowire structural element 1 according to the invention is placed between a fluid intake 102 and a fluid discharge 104. It is conceivable that in a microcatalyzer 100 of this sort gas or fluid phase reactions can be carried out. For this purpose, a gas or fluid flow is directed under pressure through the microcatalyzer 100.

The nanowire structural element 1 produced according to the invention with one or two electroconductive cover layers 26a, 26b furthermore inherently contains an electric contact to all of the nanowires connected to the electroconductive cover layer(s) 26a, 26b. As a result, a controlled voltage may be applied to the nanowires 34 thereby enabling electrocatalytic processes. Furthermore, the component may be used as an amperometric sensor.

Production of Microelements using a Radiation Mask

In accordance with the invention, it is possible to create nanowire structural elements or nanowire arrays of very small sizes, in that the template foil 12, a polymer foil in this example, is irradiated with heavy ions through a corresponding mask. The mask, e.g. a perforated mask, which is already applied, contains numerous openings or perforations, wherein each opening defines a future microelement. The mask covers the template foil 12 during the irradiation, and latent ion tracks 16 are formed thereby, which are subsequently etched to form nanopores 32 in the areas which are not covered by the mask, i.e. at the openings of the mask. The layout and the shape of the microelement are determined therefore by the mask.

This process is particularly suited to the production of many very small nanowire structural elements, as stated, in the form of microelements. The microelements 1a which may be produced in this manner consist of two cover layers, firmly joined to the nanowires, which may have a diameter of less than 500 μm, and particularly less than 100 μm, and where applicable, even less, to a size of only a few micrometers.

For example, a perforated mask for the ion irradiation with approximately 2,000 perforations on the entire deposition surface of approximately 0.5 cm$^2$ is provided, such that approximately 2,000 microelements with nanowire arrays can be created as islands in the template foil 12 at one time. After removal of the cathode layer, the microelements are separated, and break apart into individual microelements when the template foil is dissolved and removed. Additional steps may also be carried out however, e.g. in order to generate cover layers for each individual microelement.

Because all nanowires 34 within each microelement have electrical contact at both ends, the microelement with nanowire arrays is particularly suited for production of miniaturized sensors. Due to the large number of wires, not only a high sensitivity but also a defect tolerance should result thereby.

The sensor elements may be used for measuring gas flow, temperature and as a motion sensor, for example. With reference to FIG. 22, a sensor 150 of this type has at least one measuring device with a first and second microelement nanowire structural element 1a, wherein the microelement nanowire structural elements 1a in each case have cover layers 26a, 26b, wherein each of the two nanowire structural elements 1a have electrical contact through one or both of the two cover layers 26a, 26b, wherein the two nanowire structural elements 1a are contacted separately. A heating element is located between the two microelement nanowire structural elements, such as a microwire 152 which may be heated by means of applying voltage. The calibration of the resistance of the sensor element 150 is used as a measure for the gas flow rate or the change in temperature, or change in position.

It is clear to the person skilled in the art that the preceding descriptions of embodiments are to be understood as exemplary, and that the invention is not limited to said, but rather, can be varied in numerous ways, without abandoning the scope of the invention. In particular, the production of a microcatalyzer is only one of many uses for the nanowire structural element of the invention. The segmented nanowires also have many applications as individual units. Furthermore, it is clear that the characteristics, regardless of whether they are presented in the description, the claims, the illustrations or otherwise, also define significant components of the invention, even if they are described in conjunction with other characteristics.

The invention claimed is:

1. A nanowire structural element that includes:
   an array of numerous neighboring segmented nanowires of electrochemically depositioned material, including alternating sequences of numerous first segments having first diameters and numerous second segments having second diameters, wherein the first diameters are larger than the second diameters, such that the nanowires have segmented structures in the lengthwise direction, wherein the second segments form connecting pieces between the first segments, and at least one substrate layer to which the nanowires, in each case, are firmly joined,
   wherein the array includes the nanowires integrally formed to two substrate layers to define space between the substrate layers.

2. The nanowire structural element according to claim 1 wherein the array includes the nanowires extending perpendicularly between the substrate layers, wherein interconnected open spaces exist between the nanowires such that an open cell hollow chamber-like structure is defined in such a manner that a fluid can be fed therethrough.

3. A microcatalyzer including the nanowire structural element according to claim 2.

4. A nanowire structural element according to claim 1, wherein the first segments with the larger diameters have a cylindrical shape.

5. A nanowire structural element according to claim 1, wherein the first and second segments are connected as units and consist of the same electrochemically depositioned material.

6. A nanowire structural element according to claim 1, wherein the first segments with the larger diameters are longer than the second segments with smaller diameters.

7. A nanowire structural element according to claim 1, wherein the first and/or second segments have in each case consistent lengths for at least portions of the lengths of the nanowires.

8. A nanowire structural element according to claim 1, wherein the diameters of the first segments are smaller than 500 nm over the course of the lengths of the nanowires.

9. A nanowire structural element according to claim 1, wherein lengths of the first segments with larger diameters are less than 1,000 nm and/or lengths of the second segments with the smaller diameters are less than 50 nm.

10. A nanowire structural element according to claim 1, wherein the first and second segments alternate in a regular pattern over the lengths of the nanowires, such that continuously over the lengths of the nanowires there is always exactly one first segment lying between two second segments.

11. A nanowire structural element that includes:
    an array of numerous neighboring segmented nanowires, and
    two spaced cover layers to which the nanowires, in each case, are firmly joined,
    wherein the nanowires are of electrochemically deposited material, including alternating sequences of numerous first segments having first diameters and numerous second segments having second diameters, wherein the first diameters are larger than the second diameters, such that the nanowires have segmented structures in the lengthwise direction, wherein the second segments form connecting pieces between the first segments,
    wherein the nanowires extend between the two cover layers and the segmented nanowires are firmly joined with their first end to the first cover layer and with their second end to the second cover layer, such that the segmented nanowires firmly connect the two cover layers and define a space between the two cover layers,
    wherein interconnected open spaces exist between the segmented nanowires such that a stable sandwich-like nanostructure contained on two sides by the two cover layers are permeated with numerous nanowires in a column-manner and a two-dimensionally open cell hollow chamber-like structure is defined in the plane parallel to the cover layers in such a manner that between the two cover layers a fluid can be fed through the two-dimensional open cell hollow chamber-like structure.

12. A microreactor system that includes: a microstructured channel system with a fluid intake and a fluid discharge, at least one nanowire structural element in accordance with claim 11 with segmented nanowires as a reactor element between the fluid intake and the fluid discharge, such that fluid from the fluid intake can be introduced to the hollow chamber-like structure between the two cover layers, fed through the open spaces between the segmented nanowires and discharged from the hollow chamber-like structure through the fluid discharge, wherein the two-dimensional open cell hollow chamber-like structure of the nanowire structural element between the two cover layers forms a reaction volume and surfaces of the nanowires form an active surface area with which the fluid within the hollow chamber-like structure interacts during a flow-through period.

13. A catalyzer system that includes: a microstructured channel system with a fluid intake and a fluid discharge, at least one nanowire structural element in accordance with claim 11 as a catalyzer element between the fluid intake and the fluid discharge, such that fluid from the fluid intake is introduced to the hollow chamber-like structure between the two cover layers, fed through the open spaces between the segmented nanowires and then discharged from the hollow chamber-like structure through the fluid discharge, wherein the two-dimensional open cell hollow chamber-like structure of the nanowire structural element between the two cover layers forms a catalytic reaction volume and surfaces of the nanowires form a catalytic active surface with which the fluid within the hollow chamber-like structure interacts during a flow-through period.

14. A sensor element, in particular for measuring gas flow, temperature or motion, containing: at least one measuring device with a first nanowire structural element and a second nanowire structural element according to claim 11, wherein the nanowire structural elements in each case have at least one cover layer joined to the segmented nanowires for the purpose of establishing contact with the respective nanowire structural element and wherein a heating element is located between the nanowire structural elements.

\* \* \* \* \*